(12) United States Patent
Frances et al.

(10) Patent No.: US 7,740,482 B2
(45) Date of Patent: Jun. 22, 2010

(54) STABLE CATIONICALLY CROSSLINKABLE/POLYMERIZABLE DENTAL COMPOSITION WITH A HIGH FILLER CONTENT

(75) Inventors: Jean-Marc Frances, Meyzieu (FR); Martial Deruelle, Mornant (FR); Yves Giraud, Saint Foy les Lyon (FR)

(73) Assignee: Bluestar Silicones France, Lyons (FR)

( * ) Notice: Subject to any disclaimer, the term of this patent is extended or adjusted under 35 U.S.C. 154(b) by 0 days.

(21) Appl. No.: 12/149,536

(22) Filed: May 2, 2008

(65) Prior Publication Data

US 2008/0287562 A1 Nov. 20, 2008

Related U.S. Application Data

(63) Continuation of application No. 11/126,273, filed on May 11, 2005, now abandoned.

(60) Provisional application No. 60/599,064, filed on Aug. 6, 2004.

(30) Foreign Application Priority Data

May 13, 2004 (FR) .................................. 04 05177
Jun. 30, 2004 (FR) .................................. 04/07209

(51) Int. Cl.
*A61C 5/00* (2006.01)
*C08K 3/20* (2006.01)
*C08K 9/06* (2006.01)
*C08K 3/36* (2006.01)

(52) U.S. Cl. .................... 433/215; 433/218; 522/25; 522/26; 522/27; 522/29; 522/56; 522/31; 522/53; 522/48; 522/66; 522/77; 522/148; 522/170; 522/168; 522/172; 523/115; 523/116

(58) Field of Classification Search .................. 522/77, 522/148, 25, 26, 27, 29, 31, 48, 53, 66, 168, 522/170, 172, 56; 106/35; 523/115, 116; 433/215, 218
See application file for complete search history.

(56) References Cited

U.S. PATENT DOCUMENTS

| | | | | | |
|---|---|---|---|---|---|
| 4,775,520 | A | * | 10/1988 | Unger et al. | 423/335 |
| 4,791,213 | A | * | 12/1988 | Gawne et al. | 549/27 |
| 4,795,796 | A | * | 1/1989 | Haubennestel et al. | 528/28 |
| 5,693,688 | A | * | 12/1997 | Priou | 522/25 |
| 5,808,108 | A | * | 9/1998 | Chappelow et al. | 549/335 |
| 6,245,828 | B1 | * | 6/2001 | Weinmann et al. | 522/148 |
| 6,302,926 | B1 | * | 10/2001 | Anselmann et al. | 23/313 R |
| 6,362,251 | B1 | * | 3/2002 | Alkemper et al. | 523/116 |
| 6,509,409 | B1 | * | 1/2003 | Thetford | 524/589 |
| 6,632,853 | B2 | * | 10/2003 | Alkemper et al. | 522/83 |
| 6,747,071 | B1 | * | 6/2004 | Frances | 522/148 |
| 6,779,656 | B2 | * | 8/2004 | Klettke et al. | 206/219 |
| 2003/0055167 | A1 | * | 3/2003 | Klee et al. | 525/100 |
| 2006/0004121 | A1 | * | 1/2006 | Ding et al. | 523/115 |

OTHER PUBLICATIONS

WO 00/19967, Jean-Marc Frances, "Dental Composition Based on Silicone Crosslinkable by Cation Process", Apr. 2000.*

* cited by examiner

*Primary Examiner*—Susan W Berman
(74) *Attorney, Agent, or Firm*—Buchanan Ingersoll & Rooney, P.C.

(57) ABSTRACT

Stable and substantially filled cationic dental compositions are described which include:
  (1) at least one cationically reactive compound (A);
  (2) at least one dental filler (B);
  (3) optionally, at least one dispersant (C) composed of at least one organic polymer or copolymer;
  (4) at least one cationic photoinitiator (D); and
  (5) optionally, at least one photosensitizer (E). The dental filler (B) is treated with at least one organosilicon coupling agent (F), and
at least one compound (G). The organosilicon coupling agent (F) has at least one reactive function (rfA) directly linked to a silicon atom forming after activation of a chemical bond with the dental filler, and at least one reactive function (rfB) not directly linked to a silicon atom, forming after activation, a chemical bond with a reactive function (rfC) of the compound (G).

37 Claims, No Drawings

STABLE CATIONICALLY CROSSLINKABLE/POLYMERIZABLE DENTAL COMPOSITION WITH A HIGH FILLER CONTENT

CROSS-REFERENCE TO PRIORITY/PCT/PROVISIONAL APPLICATIONS

This application is a continuation of U.S. application Ser. No. 11/126,273 now abandoned which filed on May 11, 2005 claims priority under 35 U.S.C. §119 of French Application No. 04/05177, filed May 13, 2004, and French Application No. 04/07209, filed June 30, 2004, and of provisional application No. 60/599,064, filed Aug. 06, 2004, each hereby expressly incorporated by reference and each assigned to the assignee hereof.

BACKGROUND

1 Filed of the Invention

The field of the invention is that of dental compositions. More specifically, the dental compositions developed in the context of the present invention may be used for making dental prostheses and for dental restoration.

2 Related Art

These dental compositions are conventionally epoxy resins, or photopolymerizable silicones or free-radical-polymerizable acrylate resins. These compositions also include particulate reinforcing fillers (e.g. hydrophobicized silica), photoinitiators and optionally photosensitizers or even other functional additives such as pigments or stabilizers.

Once mixed together, these compositions are shaped and then photocrosslinked into a mass whose structure is similar to that of teeth.

The fact that the filler consists of very fine particles ($\approx 0.01$ to 5 μm) with a large specific surface area is a factor that limits its degree of incorporation into the resin. The reason for this is that said resin has a limited absorption capacity. As a result, the filler contents of such compositions rarely reach more than 45% by volume. This therefore penalizes the mechanical reinforcing function assigned to the particulate filler.

Furthermore, dental compositions are formulated with reinforcing fillers such as mineral glasses or combustion silicas of very low particle size, the surface silanols and/or residual water of which react with the cationic functions, preventing the compositions from being stored. This is also the case when these glasses or these combustion silicas are pretreated with silanes, for instance glycidyloxypropyltrimethoxysilane or glycidyloxypropyltriethoxysilane, or even methacryloxypropyltrimethoxysilane. Reinforcing fillers interact with the reactive functions of the (photo)polymerizable/crosslinkable species and are thus the cause of instability problems of the dental composition during its storage, which may be up to several months. This phenomenon of instability on storage is accentuated for substantially filled compositions (i.e. overall filler content ≧50%).

U.S. Pat. No. 6,306,926 concerns dental compositions based on epoxy resins (e.g. UVR® 6105, EPON® 828, GY281®), oxetane or vinyl ether, inter alia, which are polymerizable/crosslinkable, cationically and under irradiation, and optionally free-radical-polymerizable (meth)acrylate resins. Besides polymerization inducers such as cationic photoinitiators and optionally free-radical initiators, depending on the case, these compositions comprise a radio-opaque microparticulate mineral filler selected from the following metallic compounds: oxides, halides, borates, phosphates, silicates, carbonates, germanates, tetrafluoroborates, hexafluorophosphates, having an isoelectric point of less than 7. This composition is such that its Barcol hardness is at least 10, after 30 minutes of cationic polymerization at 25° C.

These resins have the drawback of not being fully transparent to the actinic radiation for activation of the polymerization via UV-visible radiation, which is harmful to the reaction kinetics and thus limits the possibilities of obtaining very thick photocrosslinked materials.

Patent application FR-A-2 784 025 is directed toward overcoming this problem by proposing dental compositions based on silicone resins that are polymerizable/crosslinkable, cationically and under irradiation, possibly followed by thermal post-crosslinking. These silicone resins contain oxirane (epoxide, oxetane, etc.) or vinyl ether functionalities. Such compositions comprise:

one or more cationically crosslinkable and/or polymerizable polydimethylsiloxanes bearing on at least one of their ends reactive functions of formula:

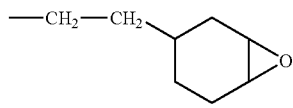

an effective amount of at least one initiator of onium borate type:

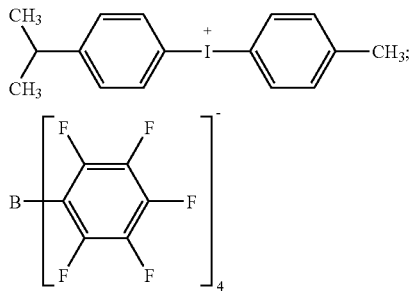

at least one photosensitizer, and at least one dental filler or inert reinforcing filler based on dental glasses or on polymethyl methacrylate or on combustion silica optionally treated with hexamethyldisilazane or polydimethylsiloxane with a specific surface area of 200 m²/g.

These dental compositions are intended for the manufacture of dental prostheses or appliances and for dental restoration.

These silicones have the advantage over cationically crosslinking organic resins of being highly transparent to UV-visible light and thus of allowing very thick (several millimeters thick) photocrosslinked materials to be obtained in a very short time (less than one minute) with a UV lamp that emits in the visible range >400 nm.

However, these silicones are formulated with reinforcing fillers of Lewis acid or Brönsted acid nature, such as ground glasses or combustion silicas of very low particle size, the surface silanols and/or the residual water of which react with the cationic functions. Such silicone formulations are therefore unstable on storage. Furthermore, when these silicones are formulated with photosensitizers of thioxanthone type, large chromatic variation is observed during exposure for crosslinking purposes. This is reflected by a pinkish coloration of the finished product (after exposure) which is not esthetically desirable.

Besides these problems, these silicone dental compositions remain to be improved as regards increasing the filler content, so as to allow an improvement in the mechanical properties.

Substantially filled dental compositions, presented as having good mechanical properties and comprising from 10% to 70% by volume of filler (e.g. combustion silica) with a particle size (Φm) of between 0.05 and 0.5 μm (less than 50% by volume of particles of diameter Φ>0.50 μm), a free-radical-photopolymerizable acrylic monomer and a dispersant of phosphoric acid ester type of formula:

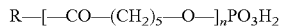

are moreover known, through patent application EP-A-1 050 291.

Such a teaching relating to free-radical dental compositions cannot in any way be transposed to silicone-based cationic dental compositions. The reason for this is that the dispersants R—[—CO—(CH$_2$)$_5$—O—]$_n$PO$_3$H$_2$ are not suitable for cationic compositions, especially since they contain a large acidic residue RPO$_3$H$_2$ that reacts in the presence of oxirane functions and harms the stability of the composition.

It is thus seen that the prior art does not provide a satisfactory solution to the twofold problem of stability on storage of dental compositions based on units that are polymerizable cationically under UV (for example oxiranes) and of dispersion of large amounts of fillers in the resin. Furthermore, the prior art does not provide a solution either to the problem of the residual coloration of dental compositions after crosslinking.

SUMMARY OF THE INVENTION

One of the essential objectives of the present invention is thus to overcome this by providing novel dental compositions based on units that are polymerizable cationically under UV (for example oxiranes), which do not have the drawbacks of the prior art as regards the stability on storage and the limited filler content.

Another essential objective of the present invention is to provide novel cationic dental compositions that are polymerizable and/or crosslinkable in an oral environment, which are not only stable on storage and substantially filled (e.g. ≧50%), but which also have the advantage of being highly transparent to UV-visible light and thus of allowing very thick (several millimeters thick) photocrosslinked materials to be obtained in a very short time (less than one minute) with a UV lamp that emits in the visible range >400 nm.

Another essential objective of the present invention is that of providing novel cationic dental compositions that are polymerizable and/or crosslinkable in an oral environment, which are stable, substantially filled (e.g. ≧50%), easy and economical to prepare, but also which do not have the drawback of generating spurious colorations after crosslinking.

Another essential objective of the present invention is that of providing a novel process for treating a reinforcing filler, in particular a dental reinforcing filler, such that it can satisfy the constraints outlined above when it is used especially as a reinforcing filler in a dental composition.

These objectives, among others, are achieved by the present invention, which relates firstly to a dental composition comprising:

(1) at least one cationically reactive compound (A);
(2) at least one dental filler (B);
(3) optionally at least one dispersant (C) comprising at least one organic polymer or copolymer;
(4) at least one cationic photoinitiator (D);
(5) and optionally at least one photosensitizer (E), said composition being characterized in that at least one dental filler (B) is treated:
a) with at least one organosilicon coupling agent (F) and
b) with at least one compound (G), said organosilicon coupling agent (F) comprising at least one reactive function (rfA) directly linked to a silicon atom reacting with the dental filler, and at least one reactive function (rfB) not directly linked to a silicon atom, reacting with a reactive function (rfC) of the compound (G).

DESCRIPTION OF PREFERRED EMBODIMENTS

In one preferred embodiment:
the reactive function (rfA) directly linked to a silicon atom of the organosilicon coupling agent (F) is an alkoxy, enoxy or hydroxyl function;
the reactive function (rfB) not directly linked to a silicon atom of the organosilicon coupling agent (F) is an oxirane, oxetane, hydroxyl, acid, carboxylic acid anhydride or diol function; and
the reactive function (rfC) of the compound (G) is an oxirane, oxetane, alkenyl ether or carbonate function.

The inventors have, to their credit, shown, surprisingly and unexpectedly, that it is possible to treat the surface of the filler and thus to increase the filler content and therefore to reinforce the material while at the same time improving the stability on storage of the composition. This stability is reflected by a shelf life of several months or years.

This technical solution is all the more advantageous since it is economically viable and easy to implement.

It is also advantageous to note that this composition is satisfactory in terms of limiting the shrinkage after polymerization/crosslinking, which is entirely noteworthy in the dental application.

According to one preferred variant of the invention, the dental composition according to the invention comprises at least one dental filler (B) treated via a process (I) comprising the following steps:

a) the dental filler (B) and at least one organosilicon coupling agent (F) comprising at least one alkoxy and/or hydroxyl function directly linked to a silicon atom and at least one oxirane, oxetane, hydroxyl, acid, carboxylic acid anhydride and/or diol function are mixed together in solvent medium, preferably in aqueous medium, b) the solvent is evaporated off to obtain an intermediate dental filler (B-1), c) the intermediate dental filler (B-1) undergoes a heat treatment so as to allow the coupling reaction between the intermediate dental filler (B-1) and the coupling agent (F) and thus to obtain an intermediate dental filler (B-2), d) the intermediate dental filler (B-2) is next mixed in solvent medium with at least one compound (G) comprising at least one oxirane, oxetane, alkenyl ether and/or carbonate function, e) the solvent is evaporated off to obtain an intermediate dental filler (B-3), and f) the intermediate dental filler (B-3) undergoes a heat treatment so as to allow the reaction between the intermediate dental filler (B-3) and the compound (G) and thus to obtain a treated dental filler (B-4).

According to another preferred variant of the invention, the heat treatment of steps c) and f) of the process (I) is performed by heating to a temperature of less than or equal to 200° C., preferably less than or equal to 165° C. and even more preferably of between 100 and 165° C.

According to one preferred embodiment, the overall content of dental fillers (B) represents up to 85% by weight and preferably between 60% and 80% by weight relative to the total weight of the dental composition.

Advantageously, the treatment of the dental filler (B) is performed with up to 20% by weight, preferably between 1% and 15% by weight and even more preferably between 2% and 10% by weight of the compound (G) relative to the total weight of the dental composition.

The treatment of the dental filler (B) with the organosilicon coupling agent (F) is preferably performed with compounds of formula:

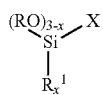
(F)

in which formula:

R is a hydrogen or a linear or branched C1-C4 alkyl or alkenyl radical, $R^1$ is a linear or branched alkyl radical or a phenyl radical, x is equal to 0, 1 or 2, and X being defined by the following formula:

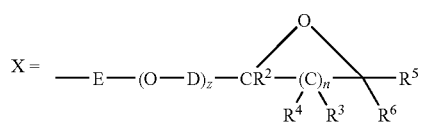
(M-1)

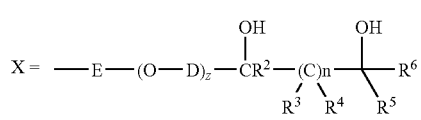
(M-2)

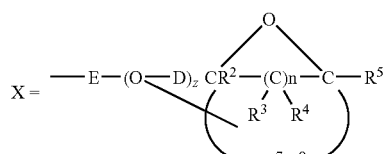
(M-3)

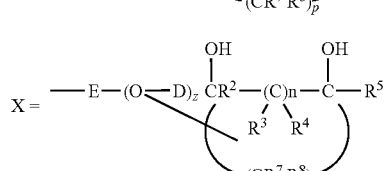
(M-4)

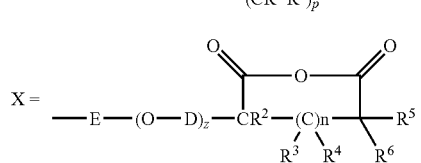
(M-5)

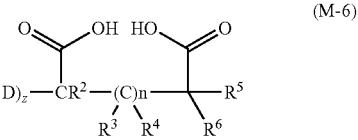
(M-6)

with:

E and D which are identical or different radicals chosen from linear or branched C1-C12 alkyls, z is equal to 0 or 1;

n is equal to 0 or 1;

is equal to 0, 1, 2, 3, 4, 5 or 6;

$R^2$, $R^3$, $R^4$, $R^5$, $R^6$, $R^7$ and $R^8$ are radicals, which may be identical or different, representing a hydrogen atom or a linear or branched C1-C12 alkyl.

Preferred organosilicon coupling agents (F) that may be mentioned include the following compounds: glycidyloxypropyltrimethoxysilane, the product of hydrolysis of glycidyloxypropyltrimethoxysilane; glycidyloxypropyltriethoxysilane, the product of hydrolysis in acidic medium of glycidyloxypropyltriethoxysilane; glycidyloxypropyldimethoxymethylsilane or the hydrolysis product, the silane β-(3,4-epoxycyclohexyl)ethyltriethoxysilane or the hydrolysis product, the silane β-(3,4-epoxycyclohexyl)ethyltrimethoxysilane or the hydrolysis product.

The treatment of the dental filler (B) with the compound (G) is preferably performed with a compound that is an organic monomer, oligomer or polymer or an organosiloxane comprising at least one oxirane, oxetane, alkenyl ether and/or carbonate function and even more preferably comprising at least one oxirane function.

Preferably, the compound (G) comprises at least one function chosen from the group consisting of the structures (M-7) to (M-12) below:

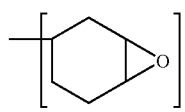
(M-7)

(M-8)

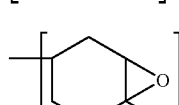
(M-9)

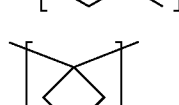
(M-10)

—(CH$_2$)$_3$—O—CH═CH$_2$;
(M-11)

—(CH$_2$)$_3$—O—CH═CH—R″
(M-12)

with R″ representing a linear or branched $C_1$-$C_6$ alkyl radical.

According to a first preferred embodiment, the compound (G) is a silicone oligomer (G-1) or a silicone polymer (G-2). The silicone oligomer (G-1) and the silicone polymer (G-2) comprise:

a) at least one unit of formula:

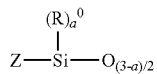
(M-13)

in which formula:

a=0, 1 or 2, $R^0$, which may be identical or different, represents an alkyl, cycloalkyl, aryl, vinyl, hydrogeno or alkoxy radical, preferably a C1-C6 lower alkyl, Z, which may be identical or different, is an organic substituent comprising at least one oxirane, alkenyl ether, oxetane and/or carbonate function, and b) at least two silicon atoms.

Advantageously, the silicone oligomer (G-1) and the silicone polymer (G-2) are chosen from the group consisting of the compounds of formulae:

a)

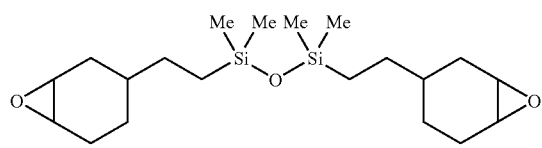
(S-1)

b)

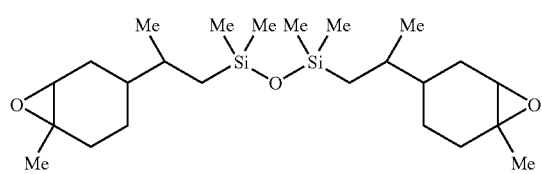
(S-2)

c)

(S-3)

d)

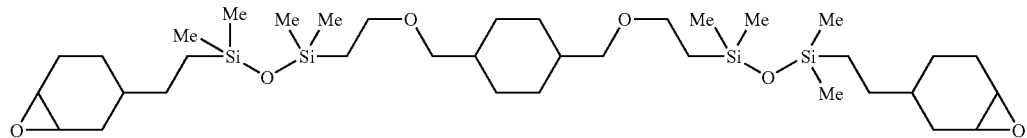
(S-4)

e)

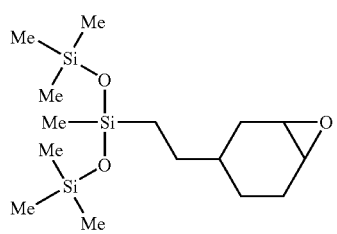
(S-5)

f)

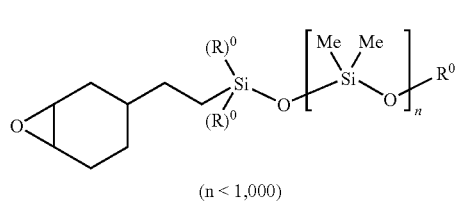
(S-6)

(n < 1,000)

-continued
g)
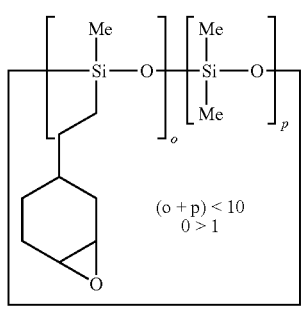
(S-7)
(o + p) < 10
o > 1
h)
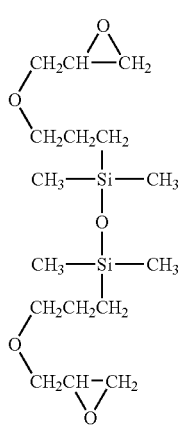
(S-8)
i)
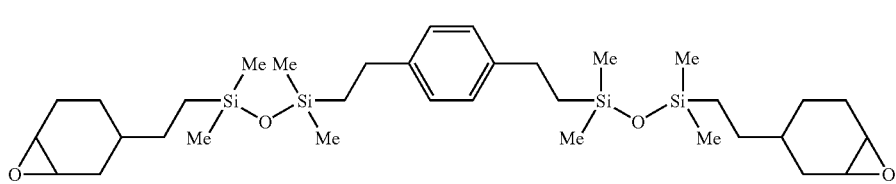
(S-9)
j)
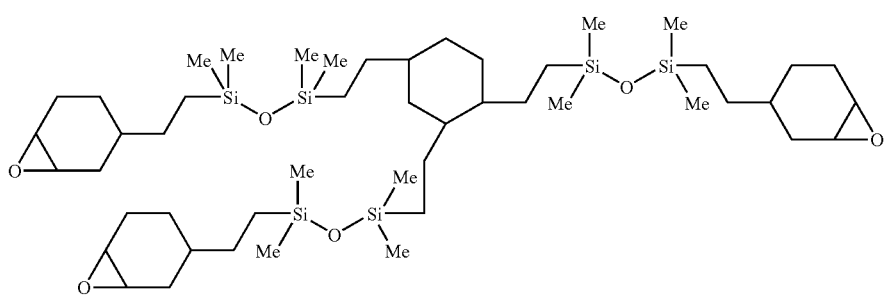
(S-10)
k)
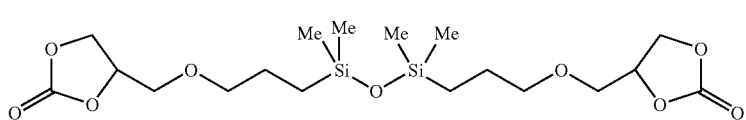
(S-11)

l)
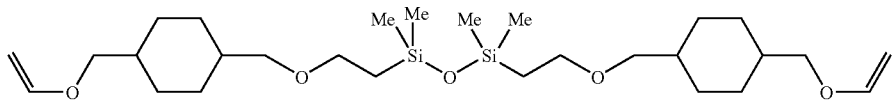
(S-12)
m)
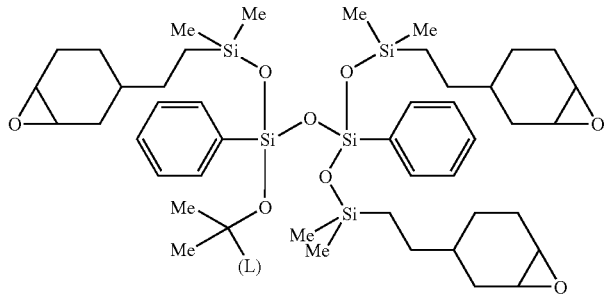
(S-13)
with L=H; OH; Me; Phenyl; C1-C12 Alkyl; C1-C6 Cycloalkyl; the groups
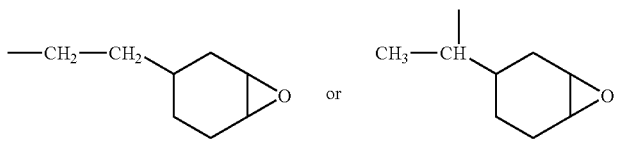
n)
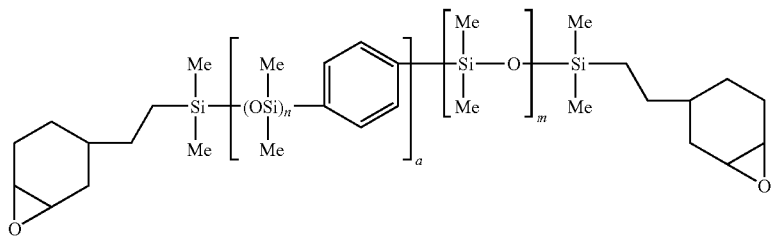
(S-14)
with n<100; a<100 and m<100
o)
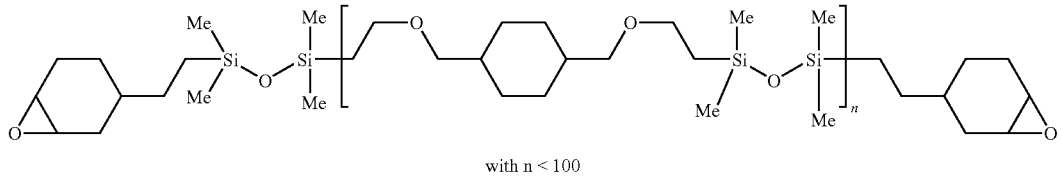
(S-15)
with n < 100
in which formulae $R^o$ or $R_0$, which may be identical or different, represents an alkyl, cycloalkyl or aryl radical, preferably a C1-C6 lower alkyl.

(S-16)
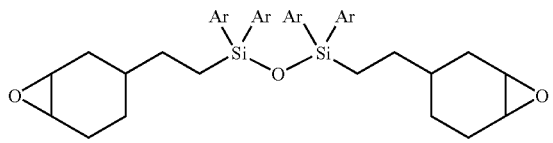
(S-17)
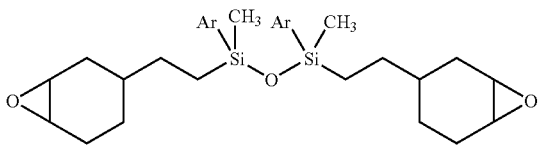
(S-18)
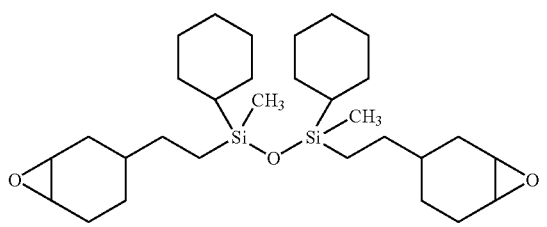
(S-19)
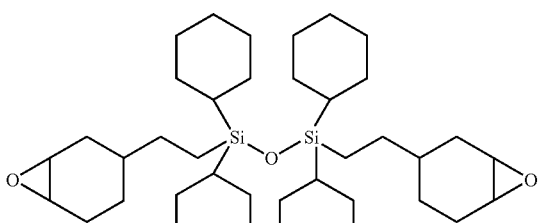
(S-20)
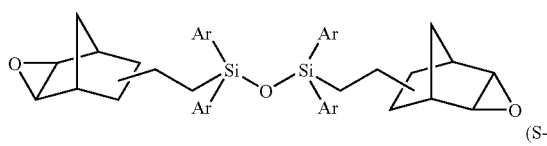
(S-21)
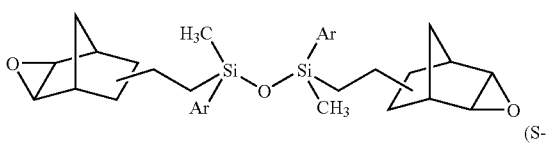
(S-22)
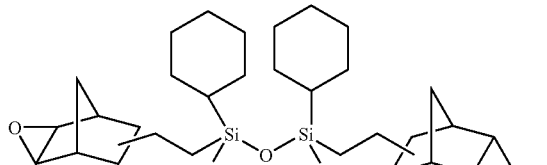
(S-23)
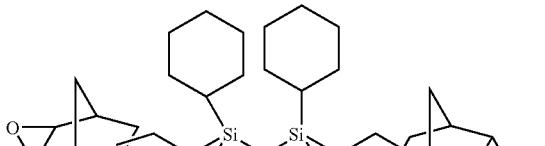
(S-24)
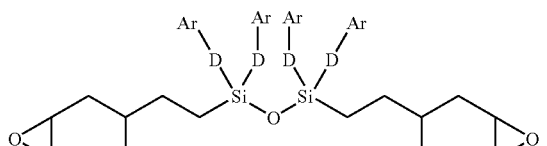
(S-25)
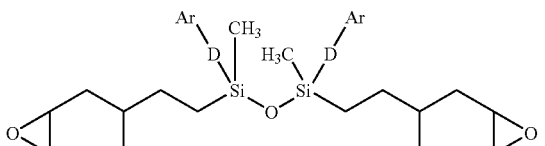
(S-26)
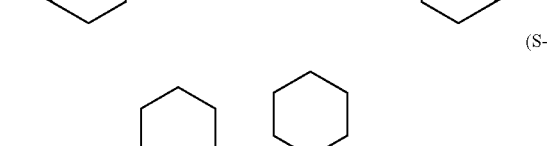
(S-27)
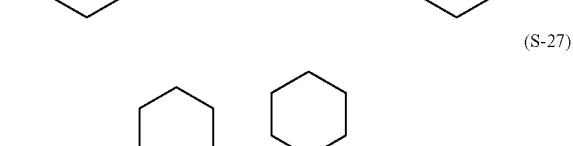
(S-28)
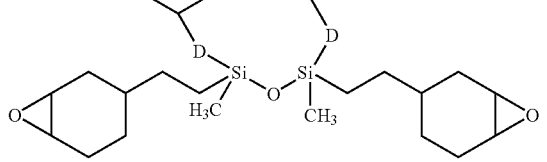
(S-29)
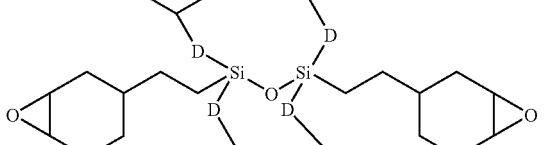
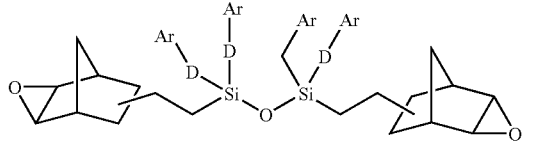
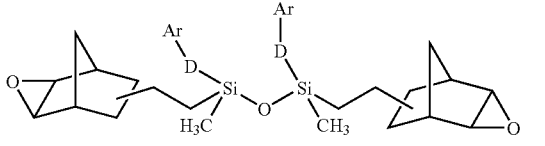

-continued
(S-30)
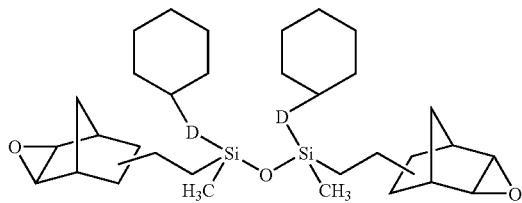
(S-31)
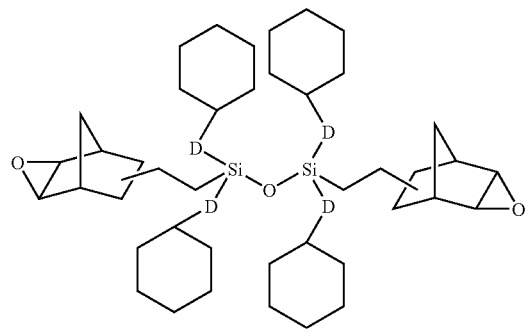
(S-32)
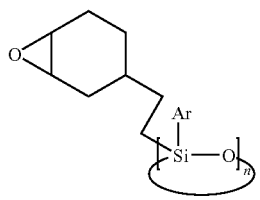
(S-33)
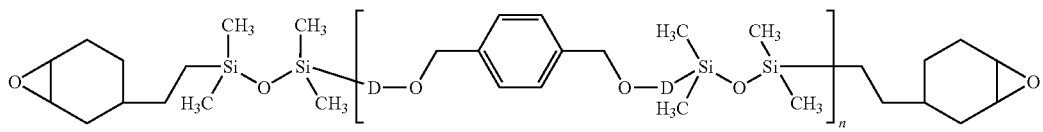
(S-34)
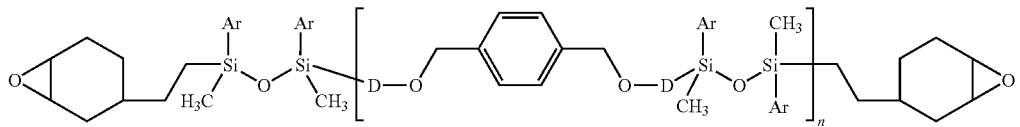
(S-35)
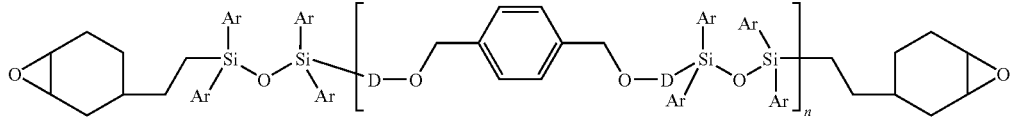
(S-36)
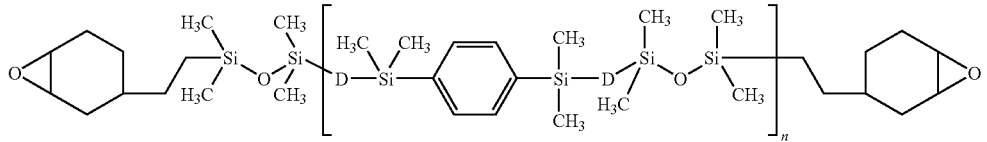
(S-37)
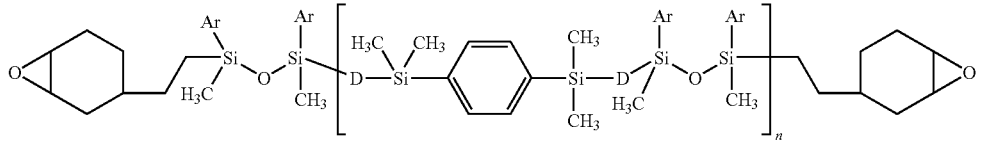
(S-38)
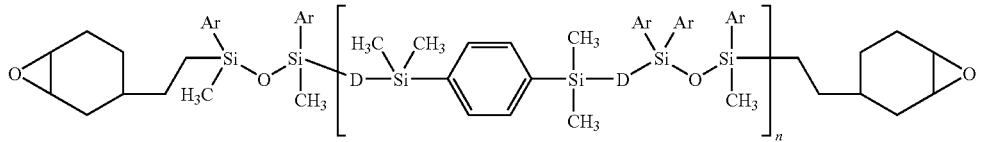
(S-39)
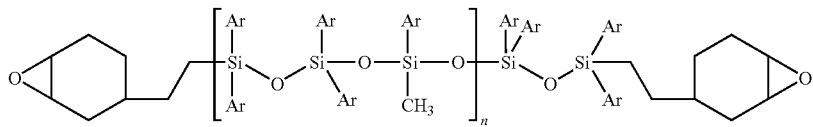

(S-40)
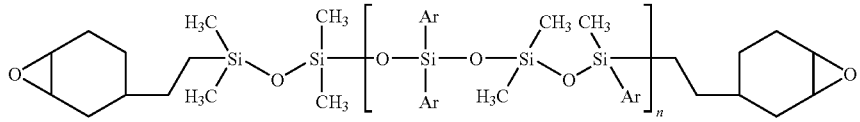
(S-41)
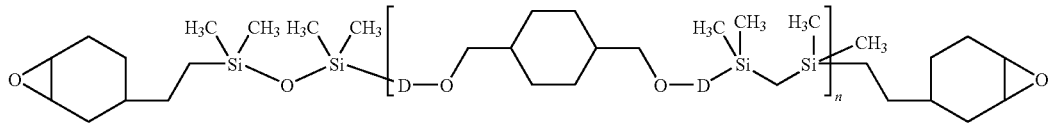
(S-42)
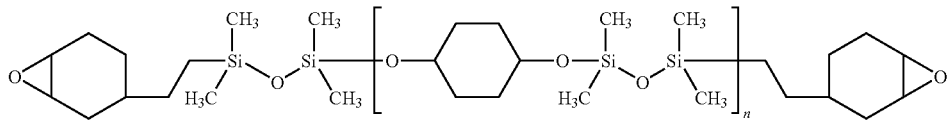
(S-43)
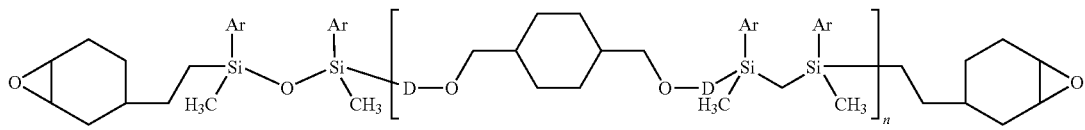
(S-44)
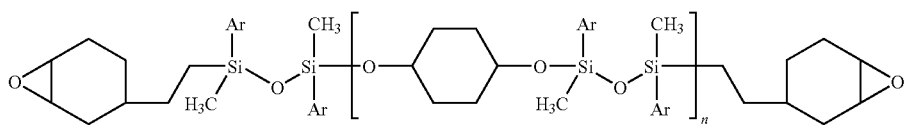
(S-45)
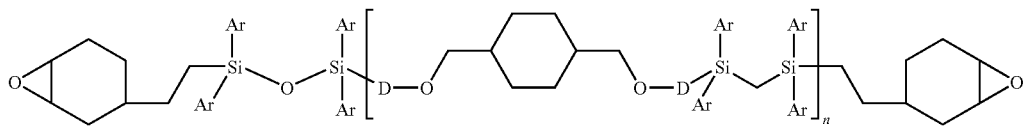
(S-46)
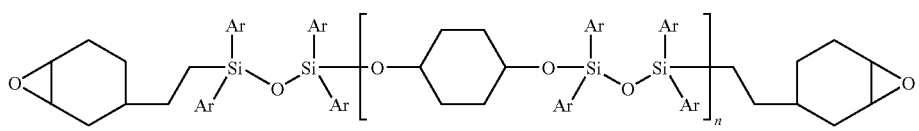
(S-47)
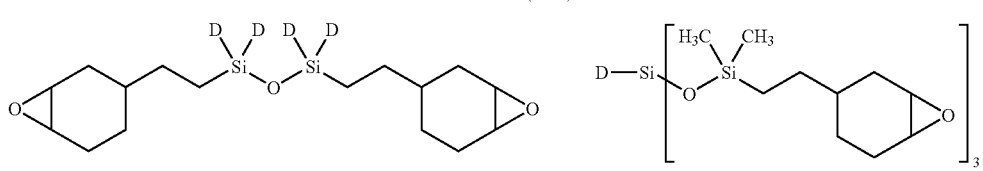
(S-48)
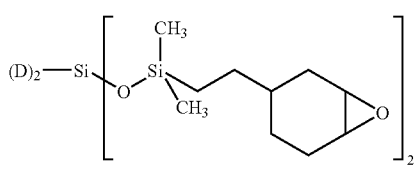
(S-49)
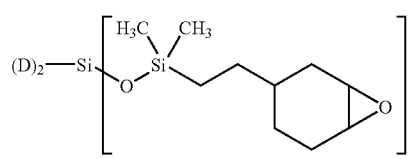
(S-50)
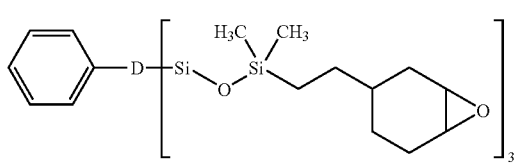
S51
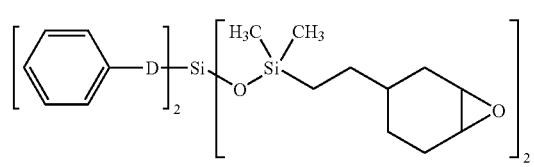
S52

-continued
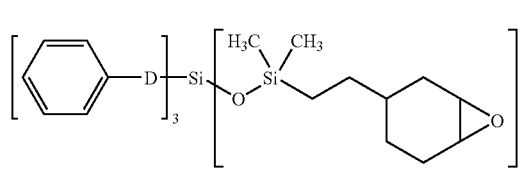
S53
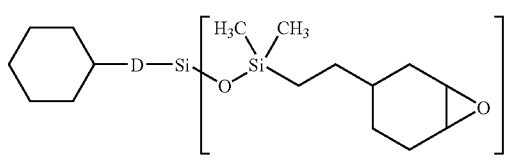
S54
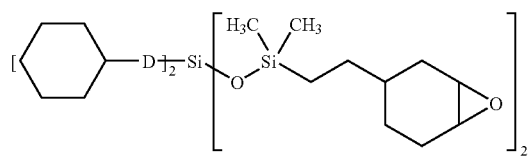
S55
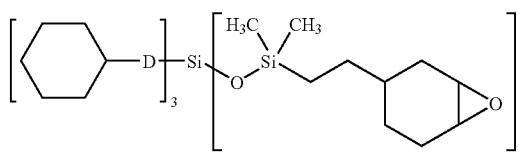
S56
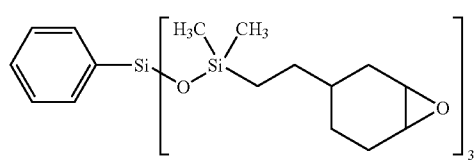
S57
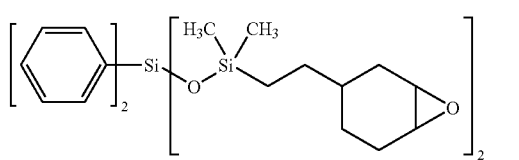
S58
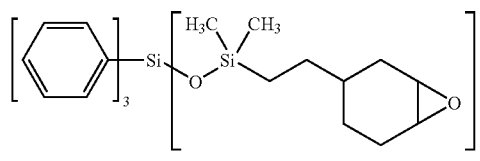
S59
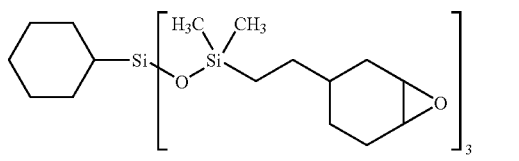
S60
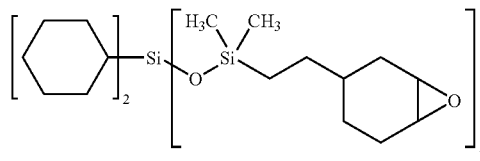
S61
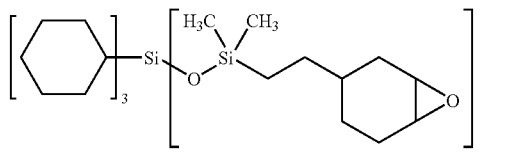
S62
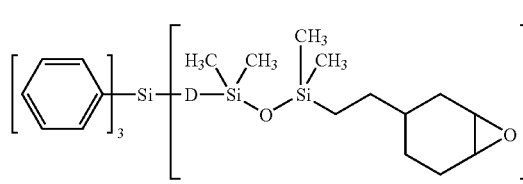
S63
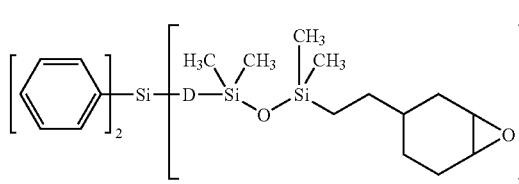
S64
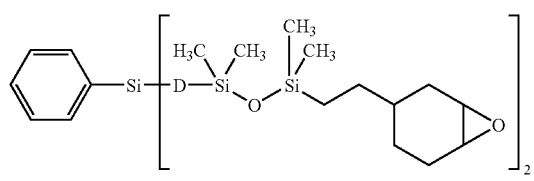
S65
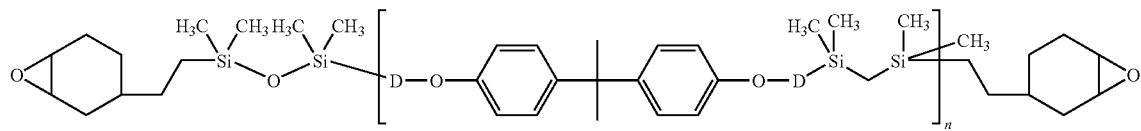
S66

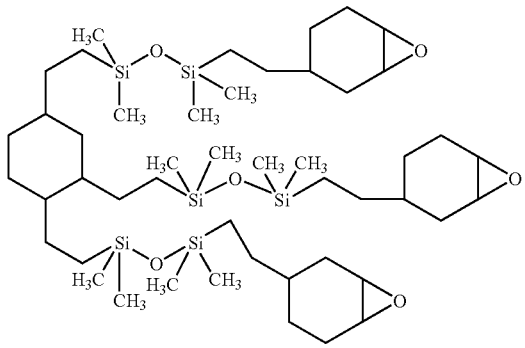
S67
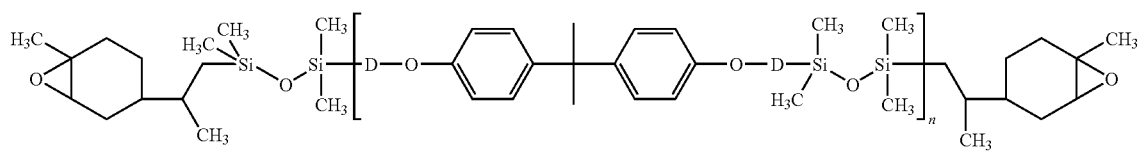
S68
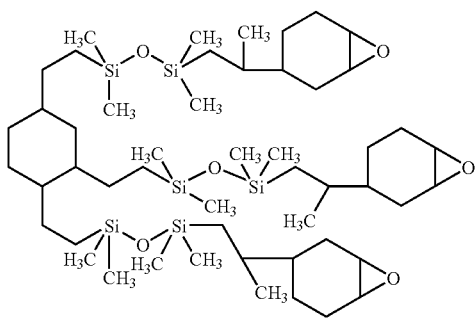
S69
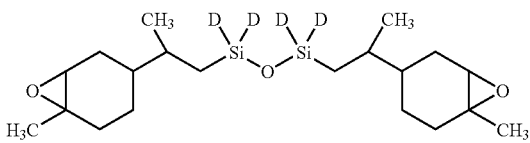
S70
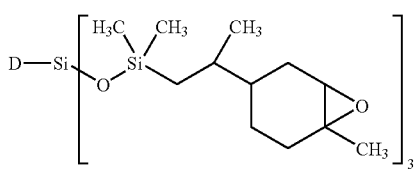
S71
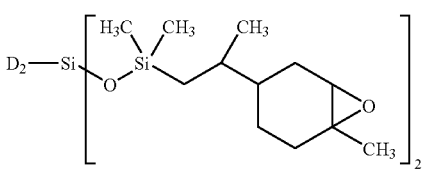
S72
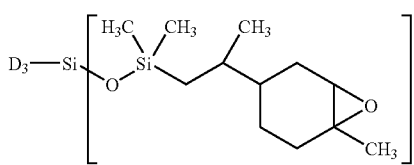
S73
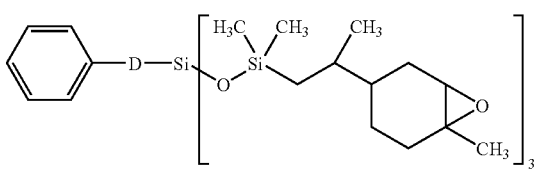
S74
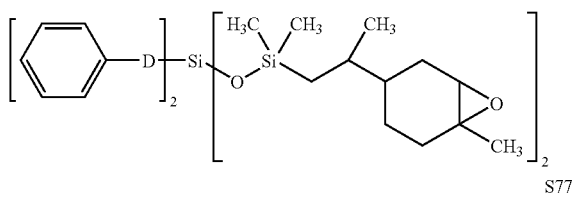
S75
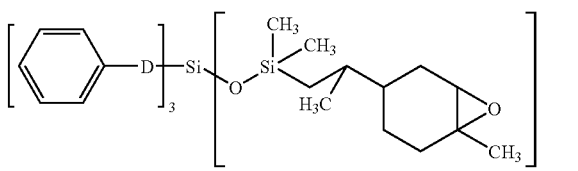
S76
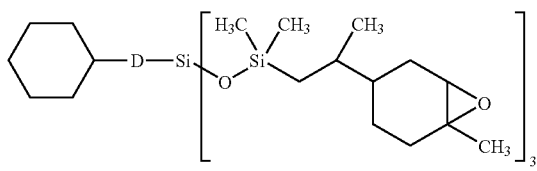
S77
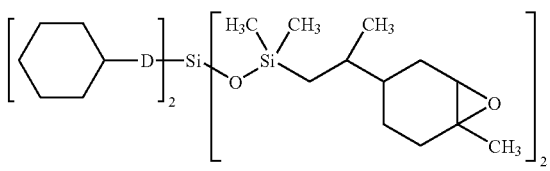
S78

-continued
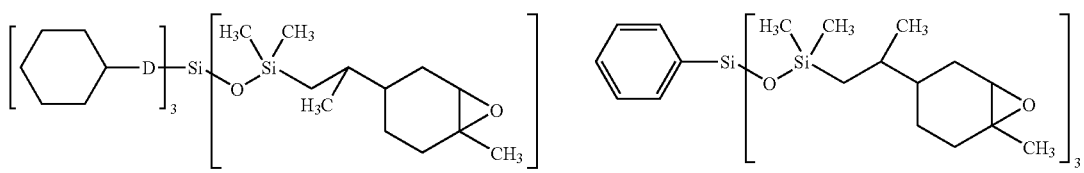
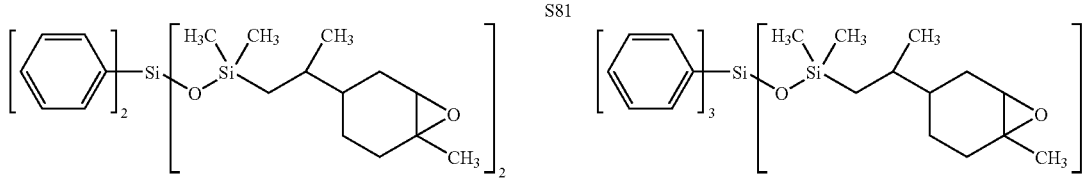
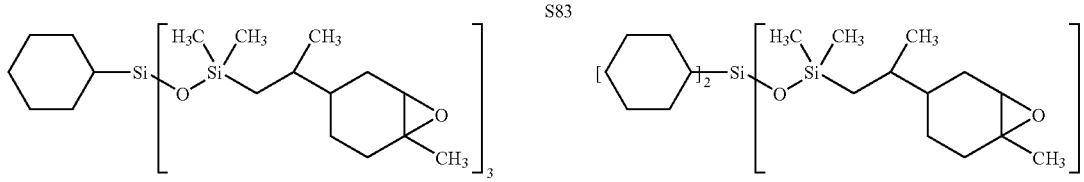
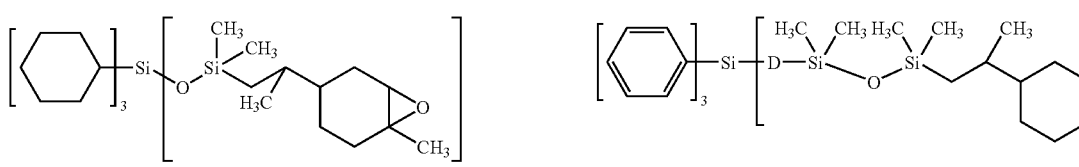
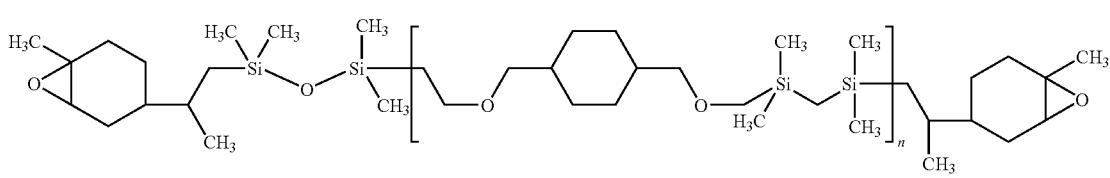
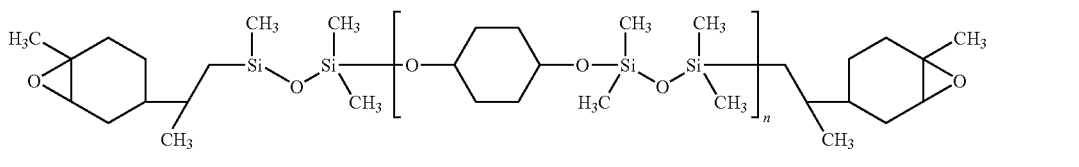
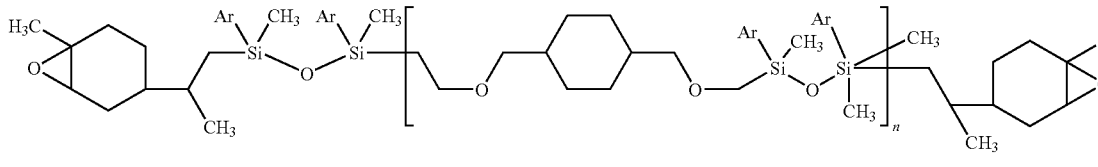
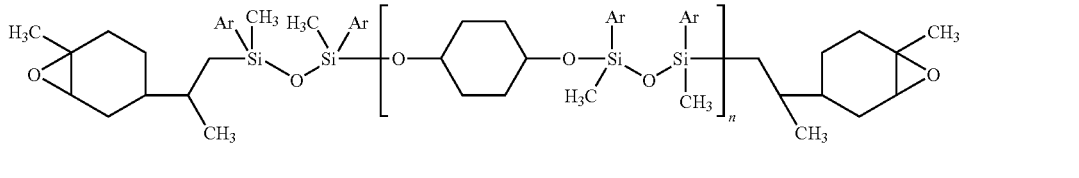
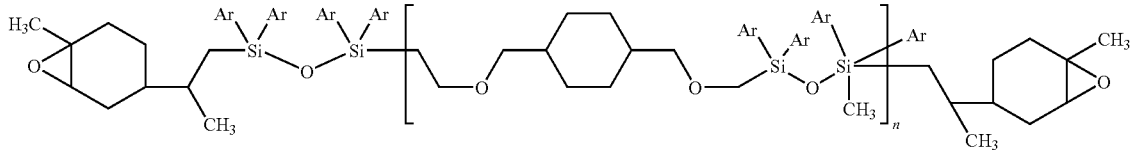

-continued

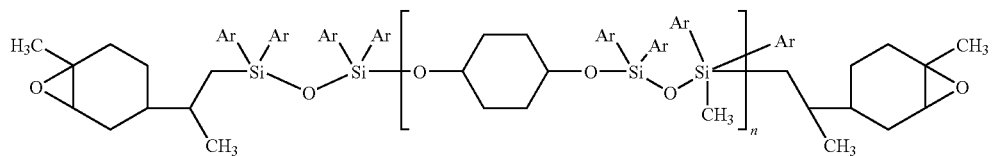
S92 in which formulae the group D is a linear or branched C1-C12 alkyl and n is an integer between 1 and 20 (limits inclusive), with Ar=aryl group.

According to a second preferred embodiment, the compound (G) is a silane (G-3) of formula:

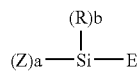

in which formula:

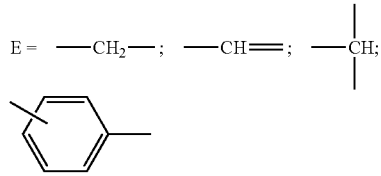

R, which may be identical or different, represents an alkyl, cycloalkyl, aryl, vinyl, hydrogeno or alkoxy radical, preferably a C1-C10 lower alkyl, Z, which may be identical or different, is an organic substituent comprising at least one oxirane, alkenyl ether, oxetane and/or carbonate function, and a+b=3.

According to one preferred embodiment, the silane (G-3) is chosen from the group consisting of the molecules (S-93) to (S-95):

According to another preferred embodiment, the compound (G) is an organic compound (G-4) chosen from the group consisting of the molecules (S-96) to (S-104):

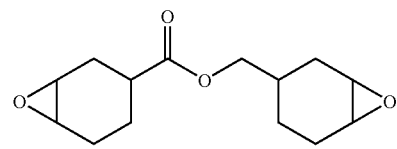
(S-96)

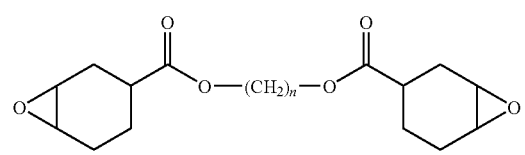
(S-97)

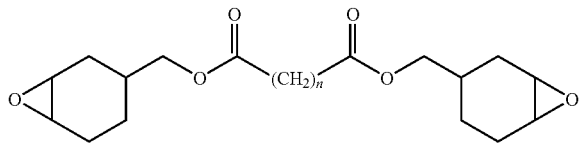
(S-98)

in which formulae: n is an integer between 1 and 10 (limits inclusive),

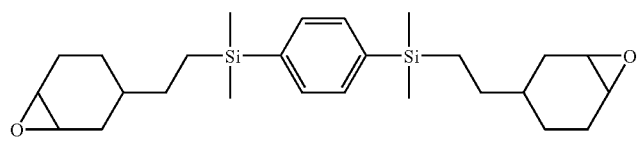
(S-93)

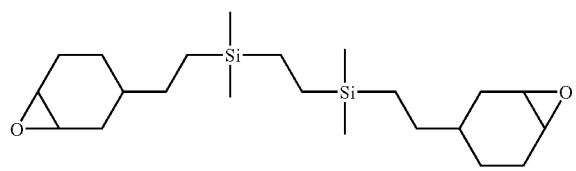
(S-94)

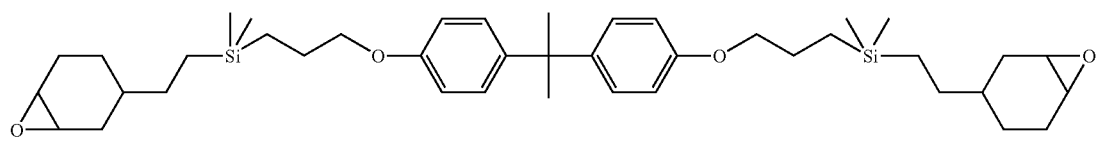
(S-95)

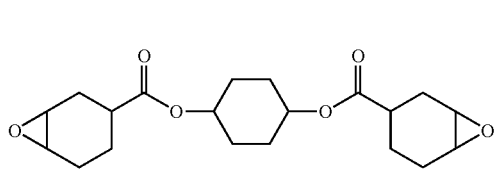
(S-99)

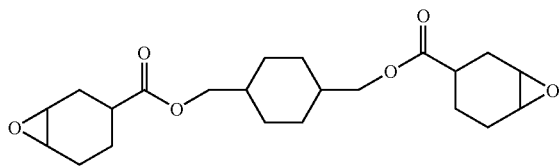
(S-100)

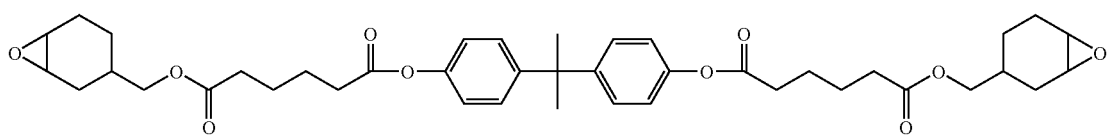
(S-101)

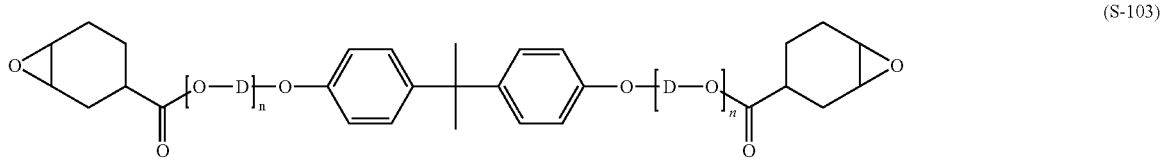
(S-103)

with n<100 and D=linear or branched C1-C12 alkyl.

Among the molecules of the type (S-103), the resin UVR6150® sold by the company Dow Chemical may be chosen.

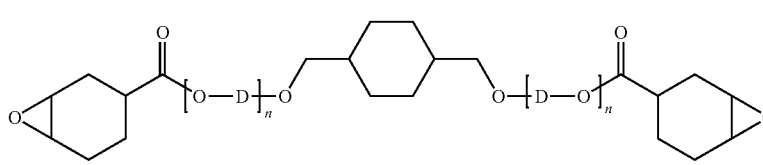
(S-104)

with n<100 and the group D=linear or branched C1-C12 alkyl.

For the resins of type (S-104), the one in which n=0 is particularly suitable for the invention.

In general, the photochemical activation is performed under UV radiation. More particularly, a UV radiation with a wavelength of about from 200 to 500 nm is used for making dental prostheses and a UV-visible radiation with a wavelength of greater than 400 nm is used for making restoration materials. A wavelength of greater than 400 nm allows crosslinking and/or polymerization in an oral environment.

The actinic (photochemical) activation may advantageously be completed (or even replaced) with thermal activation.

Preferably, the cationically reactive compound (A) is chosen from the group of monomers and/or (co)polymers comprising:

epoxys, vinyl ethers, oxetanes, spiroorthocarbonates, spiroorthoesters and combinations thereof.

Even more preferably, the cationically reactive compound (A) is a silicone oligomer (G-1), a silicone polymer (G-2), a silane (G-3) or an organic compound (G-4) as defined above by the unit (M-13), or the molecules (S-1) to (S-101).

In formula (M-13), the reactive functions Z that are particularly advantageous comprise at least one reactive function chosen from the following radicals:

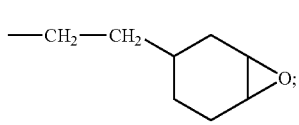
(R-1)

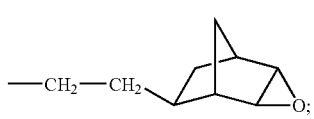
(R-2)

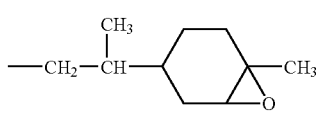
(R-3)

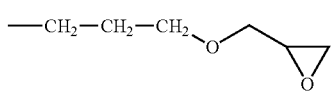
(R-4)

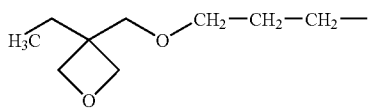
(R-5)

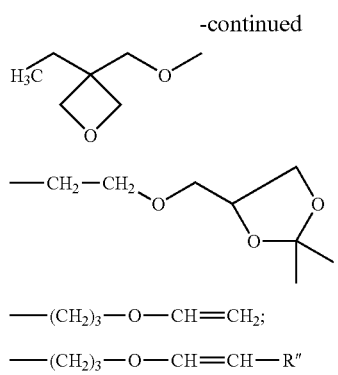

(R-6)

(R-7)

—(CH$_2$)$_3$—O—CH═CH$_2$;  (R-8)

—(CH$_2$)$_3$—O—CH═CH—R″  (R-9)

with R″ representing a linear or branched C1-C6 alkyl radical.

According to one advantageous variant, the cationically reactive compound (A) is combined with an organic epoxy resin or oxetane representing less than 80% by mass of the fraction. Among the chosen functional organic resins that will be preferred are those for which the mass percentage of reactive function is less than 20% and preferably less than 15%. The volume shrinkage will be all the more reduced during the polymerization. The resins that will preferably be selected are those of formulae (S-103) and (S-104):

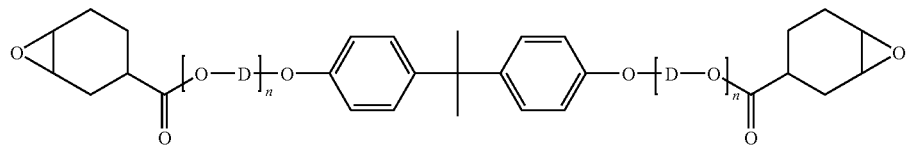
(S-103)

with n<100 and D=linear or branched C1-C12 alkyl.

Among the resins of (S-103) type that may be chosen is the resin UVR6150® sold by the company Dow Chemical.

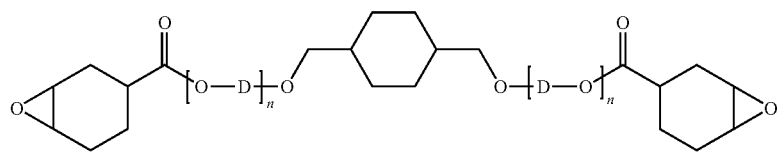
(S-104)

with n<100 and the group D=linear or branched C1-C12 alkyl.

For the resins of (S-104) type, the one in which n=0 is particularly suitable for the invention.

Various types of dental filler (B) may be used to prepare the compositions according to the invention. The fillers are chosen as a function of the final use of the dental composition: these fillers affect important properties such as the appearance, the penetration of UV radiation, and also the mechanical and physical properties of the material obtained after crosslinking and/or polymerization of the dental composition.

Reinforcing fillers that may be used include treated or untreated pyrogenic silica fillers, amorphous silica fillers, quartz, glasses or non-vitreous fillers based on silicon oxides, for example of the type described in U.S. Pat. No. 6,297,181 (barium-free), zirconium, barium, calcium, fluorine, aluminum, titanium, zinc, borosilicates, aluminosilicates, talc, spherosil, ytterbium trifluoride, polymer-based fillers in the form of ground powder such as inert or functionalized polymethyl methacrylates, polyepoxides or polycarbonates, ceramic whiskers (Si—C, Si—O—C, Si—N, Si—N—C, Si—N—C—O) and glass fibers.

Examples that will be mentioned include:

inert fillers based on polymethyl methacrylate Luxaself® from the company UGL, which may be used in the dental field and pigmented pink, combustion silica fillers treated with hexamethyldisilazane or polydimethylsiloxane, with a specific surface area of 200 m$^2$/g, untreated combustion silica fillers (Aerosil-AE200® sold by the company Degussa), quartz or glasses based on silicon oxides.

According to one embodiment of the invention, the dental filler (B) is a mineral glass or a combustion silica.

According to one advantageous characteristic of the invention, the dental fillers (B) represent up to 85% by weight, preferably between 50% and 85% by weight and even more preferably between 60% and 85% by weight relative to the total weight of the dental composition.

In accordance with the invention, the dispersant (C) is selected from the group comprising: polyurethane/acrylate copolymers optionally salified with an alkylammonium, acrylic copolymers optionally salified with an alkylammonium, carboxylic acid monodiesters, polyesters, polyethers, polyurethanes, modified polyurethanes, polyol-polyacrylates, copolymers thereof or mixtures thereof. The dispersants sold under the brand name Disperbyk® (from the company Byk) or Solsperse® (from the company Avecia) are particularly suitable for the invention. Examples that may be mentioned in particular include the commercial products: Disperbyk® 164, Disperbyk® 161, Disperbyk® 166, Disperbyk® 2070, Disperbyk® 9075, Disperbyk® 9076. Mention may also be made of the dispersants cited in the following patents:

U.S. Pat. No. 5,882,393 describing dispersants based on polyurethanes/imidazoles-acrylates or epoxies;

U.S. Pat. No. 5,425,900 describing polyurethane-based dispersants;

U.S. Pat. No. 4,795,796 describing dispersants based on polyurethanes/polyoxyalkylene glycol monoalkyl ether;

patent application WO-A-99/56864 describing dispersants based on polyurethanes/poly(oxy-alkylene-carbonyl): ε-caprolactone and δ-valerolactone derivatives; and patent EP-B-0 403 197 describing dispersants of grafted polyol-polyacrylate type comprising a polyurethane/polyvinyl/polyacrylate random copolymer and a polyoxyalkylene polyether.

Quantitatively speaking, the dispersant (C) is present in a proportion of from 50 ppm to 1% and preferably 100 ppm to 5000 ppm.

Preferably, the amine number of the dispersant (C) is less than or equal to 60 and even more preferably between 0.1 and 50 mg of potassium hydroxide per gram of dispersant (C).

Advantageously, the acid number of the dispersant is less than or equal to 200, preferably less than or equal to 100 and even more preferably between 1 and 60 mg of potassium hydroxide per gram of dispersant.

The cationic photoinitiators (D) are chosen from onium borates (taken alone or as a mixture) of an element from groups 15 to 17 of the Periodic Table [Chem. & Eng. News, vol. 63, No. 5, 26 of Feb. 4, 1985] or of an organometallic complex of an element from groups 4 to 10 of the Periodic Table [same reference].

According to one preferred mode, the cationic photoinitiator (D) is of borate type and is chosen from those in which:

a) the cationic species of the borate is selected from:

(1) the onium salts of formula:

$$[(R^9)_n\text{-}A\text{-}(R^{10})_m]^+ \quad (I)$$

in which formula:

A represents an element from groups 15 to 17, for instance: I, S, Se, P or N, $R^9$ represents a C6-C20 carbocyclic or heterocyclic aryl radical, said heterocyclic radical possibly containing nitrogen or sulfur as hetero elements, $R^{10}$ represents $R^9$ or a linear or branched C1-C30 alkyl or alkenyl radical; said radicals $R^9$ and $R^{10}$ being optionally substituted with a C1-C25 alkoxy, C1-C25 alkyl, nitro, chloro, bromo, cyano, carboxyl, ester or mercapto group, m and n are integers, with n+m=v+1, v being the valency of the element A, (2) oxoisothiochromanium cations, in the present case those described in patent application WO 90/11303, especially the sulfonium salt of 2-ethyl-4-oxoisothiochromanium or of 2-dodecyl-4-oxoisothiochromanium and the oxoisothiochromanium cations of structural formula V:

Structure V

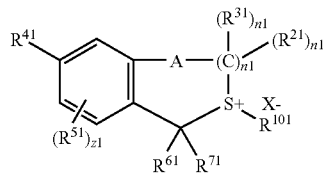

in which formula:

A represents

n1=an integer between 1 and 3;
z1=an integer between 0 and 3;

X represents a group of formula $M^1Y^1_{r1}$ (1) or of formula $Q^1$ (2) in which $M^1Y^1_{r1}$ (1): $M^1$=Sb, As, P, B or Cl, $Y^1$ represents a halogen (preferably F or Cl) or O and in which r1 is an integer between 4 and 6, the formula $Q^1$ (2) represents a sulfonic acid $R^{81}$—$SO_3$ in which $R^{81}$ is an alkyl or aryl group, or an alkyl or aryl group substituted with a halogen, preferably F or Cl, $R^{101}$ represents an alkyl or cycloalkyl group, preferably of $C_1$-$C_{20}$, or an aryl group, $R^{21}$ represents a hydrogen or an alkyl, alkenyl, cycloalkenyl or cycloalkyl group, preferably of $C_1$-$C_{20}$, or an aryl group, all the $R^{21}$ being independent of each other, $R^{31}$ represents a hydrogen or an alkyl, alkenyl, cycloalkenyl or cycloalkyl group, preferably of $C_1$-$C_{20}$, or an aryl group, all the $R^{31}$ being independent of each other, $R^{41}$ represents a hydrogen, a halogen, an alkenyl group, for example vinyl, cycloalkenyl, alkyl or cycloalkyl, preferably of $C_1$-$C_{20}$, an alkoxy or thioalkoxy group, preferably of $C_1$-$C_{20}$, a poly(alkylene oxide) group with up to 10 alkylene oxide units ending with a hydroxyl or a ($C_1$-$C_{12}$) alkyl, an aryl group or an aryloxy or thioaryloxy group, $R^{51}$ represents a halogen, an alkenyl group, for example vinyl, cycloalkenyl, alkyl or cycloalkyl group, preferably of $C_1$-$C_{20}$, an alkoxy or thioalkoxy group, preferably of $C_1$-$C_{20}$, a poly(alkylene oxide) group with up to 10 alkylene oxide units ending with a hydroxyl or a ($C_1$-$C_{12}$) alkyl, an aryl group or an aryloxy or thioaryloxy group, $R^{61}$ represents a hydrogen, an alkyl, alkenyl, cycloalkenyl or cycloalkyl group, preferably of $C_1$-$C_{20}$, or an aryl group, $R^{71}$ represents a hydrogen, an alkyl, alkenyl, cycloalkenyl or cycloalkyl group, preferably of $C_1$-$C_{20}$, or an aryl group; and (3) the organometallic salts having the following formula:

$$(L_1L_2L_3M)^{+q} \quad (II)$$

in which formula:

M represents a metal from groups 4 to 10, especially iron, manganese, chromium or cobalt, L1 represents a ligand linked to the metal M via π electrons, the ligand being chosen from the ligands $η^3$-alkyl, $η^5$-cyclopentadienyl and $η^7$-cycloheptatrienyl and the η6-aromatic compounds chosen from the optionally substituted $η^6$-benzene ligands and the compounds containing from 2 to 4 fused rings, each ring being capable of contributing to the valency layer of the metal M via 3 to 8 π electrons, L2 represents a ligand linked to the metal M via π electrons, the ligand being chosen from the $η^7$-cycloheptatrienyl ligands and the $η^6$-aromatic compounds chosen from the optionally substituted $η^6$-benzene ligands and the compounds containing from 2 to 4 fused rings, each ring being capable of contributing to the valency layer of the metal M via 6 or 7 π electrons, L3 represents from 0 to 3 identical or different ligands linked to the metal M via σ electrons, this or these ligand(s) being chosen from CO and NO2+; the total electronic charge q of the complex toward which L1, L2 and L3 contribute and the ionic charge of the metal M being positive and equal to 1 or 2; and b) those in which the anionic borate species has the formula:

$$[BX_aR_b]^- \quad (III)$$

in which formula:
a and b are integers ranging for a from 0 to 3 and for b from 1 to 4 with a+b=4,
the symbols X represent:
a halogen atom (chlorine or fluorine) with a=0 to 3, or an OH function with a=0 to 2,
the symbols R are identical or different and represent:
a phenyl radical substituted with at least one electron-withdrawing group, for instance $OCF_3$, $CF_3$, $NO_2$ or CN, and/or with at least 2 halogen atoms (most particularly fluorine), this being the case when the cationic species is an onium of an element from groups 15 to 17,
a phenyl radical substituted with at least one element or an electron-withdrawing group, especially a halogen atom (most particularly fluorine), $CF_3$, $OCF_3$, $NO_2$ or CN, this being the case when the cationic species is an organometallic complex of an element from groups 4 to 10, or
an aryl radical containing at least two aromatic nuclei, for instance biphenyl or naphthyl, optionally substituted with at least one element or an electron-withdrawing group, especially a halogen atom including fluorine, in particular, $OCF_3$, $CF_3$, $NO_2$ or CN, irrespective of the cationic species.

Without being limiting in nature, further details regarding the subclasses of onium borate and of borate of organometallic salts that are more particularly preferred in the context of the use in accordance with the invention are given hereinbelow.

According to a first preferred variant of the invention, the anionic borate species that are most particularly suitable are the following:

| | |
|---|---|
| 1': | $[B(C_6F_5)_4]^-$ |
| 2': | $[(C_6F_5)_2BF_2]^-$ |
| 3': | $[B(C_6H_4CF_3)_4]^-$ |
| 4': | $[B(C_6F_4OCF_3)_4]^-$ |
| 5': | $[B(C_6H_3(CF_3)_2)_4]^-$ |
| 6': | $[B(C_6H_3F_2)_4]^-$ |
| 7': | $[C_6F_5BF_3]^-$ |

According to a second preferred variant of the invention, the onium salts of formula (S-26) that may be used are described in many documents, especially in U.S. Pat. Nos. 4,026,705, 4,032,673, 4,069,056, 4,136,102 and 4,173,476. Among these, the following cations will be most particularly preferred:

$[(C_8H_{17})-O-(C_6H_4)-I-C_6H_5]^+$; $[C_{12}H_{25}-(C_6H_4)-I-C_6H_5]^+$; $[(C_8H_{17})_7-O-(C_6H_4))_2I]^+$ $[(C_8H_{17})-O-(C_6H_4)-I-C_6H_5]^+$; $[(C_6H_5)_2S-(C_6H_4)-O-C_8H_{17}]^+$; $[CH_3-C_6H_4-I-C_6H_4-CH_2CH(CH_3)_2]^+$; $[(C_{12}H_{25}-(C_6H_4)-I-(C_6H_4)-CH-(CH_3)_2]^+$ $[(C_{12}H_{25}-C_6H_4)_2I]^+$; $[(C_6H_5)_3 S]^+$; $[CH_3-(C_6H_4)-I-(C_6H_4)-CH(CH_3)_2]^+$ ($\eta$5-cyclopentadienyl)($\eta$6-toluene)$Fe^+$; ($\eta$5-cyclopentadienyl)($\eta$6-cumene) $Fe^+$, ($\eta$5-cyclopentadienyl)($\eta$6-methyl-1-naphthalene)$Fe^+$;

$[(C_6H_5)-S-C_6H_4-S-(C_6H_5)_2]^+$; $[(CH_3-(C_6H_4)-I-(C_6H_4)-OC_2H_5]^+$; $[(C_nH_{2n+1}-C_6H_4)_2I]^+$ (with, for the group $C_nH_{2n+1}$, n=1 to 18 is linear or branched).

According to a third preferred variant, the organometallic salts (3) of formula (S-27) that may be used are described in documents U.S. Pat. Nos. 4,973,722, 4,992,572, EP-A-203 829, EP-A-323 584 and EP-A-354 181. The organometallic salts more readily selected according to the invention are especially:

($\eta^5$-cyclopentadienyl)($\eta^6$-toluene)$Fe^+$,
($\eta^5$-cyclopentadienyl)($\eta^6$-methyl-1-naphthalene)$Fe^+$,
($\eta^5$-cyclopentadienyl)($\eta^6$-cumene)$Fe^+$,
bis($\eta^6$-mesitylene)$Fe^+$,
bis($\eta^6$-benzene)$Cr^+$ In accordance with these three preferred variants, examples of photoinitiators of the onium borate type that may be mentioned include the following products:

(P-16): $[(C_8H_{17})-O-C_6H_4-I-C_6H_5)]^+$, $[B(C_6F_5)_4]^-$;
(P-17): $[C_{12}H_{25}-C_6H_4-I-C_6H_5]^+$, $[B(C_6F_5)_4]^-$;
(P-18): $[(C_8H_{17})-O-C_6H_4)_2I]^+$, $[B(C_6F_5)_4]^-$;
(P-19): $[(C_8H_{17})-O-C_6H_4-I-C_6H_5)]^+$, $[B(C_6F_5)_4]^-$;
(P-20): $[(C_6H_5)_2S-C_6H_4-O-C_8H_{17}]^+$, $[B(C_6H_4CF_3)_4^-]$;
(P-21): $[(C_{12}H_{25}-C_6H_4)_2I]^+$, $[B(C_6F_5)_4]^-$;
(P-22): $[CH_3-C_6H_4-I-C_6H_4-CH(CH_3)_2]^+$, $[B(C_6F_5)_4]^-$;
(P-23): ($\eta$5-cyclopentadienyl)($\eta$6-toluene)$Fe^+$, $[B(C_6F_5)_4]^-$;
(P-24): ($\eta$5-cyclopentadienyl)($\eta$6-methyl-1-naphthalene)$Fe^+$, $[B(C_6F_5)_4]^-$;
(P-25): ($\eta$5-cyclopentadienyl)($\eta$6-cumene)$Fe^+$, $[B(C_6F_5)_4]^-$;
(P-26): $[C_{12}H_{25}-C_6H_4)_2I]^+$, $[B(C_6H_3(CF_3)_2]^-$;
(P-27): $[CH_3-C_6H_4-I-C_6H_4-CH_2CH(CH_3)_2]^+$, $[B(C_6F_5)_4]^-$;
(P-28): $[CH_3-C_6H_4)-I-C_6H_4-CH_2CH(CH_3)_2]^+$, $[B(C_6H_3(CF_3)_2)_4]^-$; and
(P-29): $[CH_3-C_6H_4-I-C_6H_4-CH(CH_3)_2]^+$, $[B(C_6H_3(CF_3)_2)_4]^-$.

As another literature reference for defining the onium borates (1) and (2) and the borates of organometallic salts (3), mention may be made of all of the content of patent applications EP 0 562 897 and 0 562 922. This content is incorporated in its entirety into the present description by reference.

As another example of an onium salt that may be used as photoinitiator, mention may be made of those disclosed in U.S. Pat. Nos. 4,138,255 and 4,310,469.

It is also possible to use other cationic photoinitiators, e.g.: iodonium hexafluorophosphate or hexafluoroantimonate salts, such as:

—$[CH_3-[(C_6H_4)-I-[(C_6H_4)-CH(CH_3)_2]^+[PF_6]^-$;
—$[CH_3-(C_6H_4)-I-(C_6H_4)-CH_2CH(CH_3)_2]^+$ $[PF_6]^-$; —$[(C_{12}H_{25}-C_6H_4)_2I]^+[PF_6]^-$ or
the ferrocenium salts of these various anions.

The photosensitizer contained within the dental composition according to the invention may be of very varied nature. In the context of the invention, it corresponds especially to one of the formulae (IV) to (XXIV) below:

formula (IV)

in which:
when n=1, $Ar^1$ represents an aryl radical containing from 6 to 18 carbon atoms, a tetrahydronaphthyl, thienyl, pyridyl or furyl radical or a phenyl radical bearing one or more substituents chosen from the group consisting of F, Cl, Br, CN, OH, linear or branched $C_1$-$C_{12}$ alkyls, —$CF^3$, —$OR^{13}$, —OPhenyl, —$SR^{13}$—SPhenyl, —$SO_2$Phenyl, —$COOR^{13}$, —O—($CH_2$—CH=$CH_2$), —O($CH_2H_4$—O)$_m$—H, —O($C_3H_6$O)$_m$—H, m being between 1 and 100, when n=2, $Ar^1$ represents a $C_6$-$C_{12}$ arylene radical or a phenylene-T-phenylene radical, in which T represents —O—, —S—, —$SO_2$— or —$CH_2$—, X represents a group —$OR^{14}$ or —$OSiR^{15}(R^{16})_2$ or forms, with $R^{11}$, a group —O—$CH(R^{17})$—, $R^{11}$ represents a linear or branched $C_1$-$C_8$ alkyl radical that is unsubstituted or that bears a group —OH, —$OR^{13}$, $C_2$-$C_8$ acyloxy, —$CF^3$ or —CN, a $C_3$ or $C_4$ alkenyl radical, a $C_6$ to $C_{18}$ aryl radical or a $C_7$ to $C_9$ phenylalkyl radical, $R^{12}$ has one of the meanings given for $R^{11}$ or represents a radical —$CH_2CH_2R^{18}$, or alternatively forms with $R^{11}$ a $C_2$-$C_8$ alkylene radical or a $C_3$-$C_9$ oxa-alkylene or aza-alkylene radical, $R^{13}$ represents a lower alkyl radical containing from 1 to 12 carbon atoms, $R^{14}$ represents a hydrogen atom, a $C_1$-$C_{12}$ alkyl radical, a $C_2$-$C_6$ alkyl radical bearing a group —OH, —$OR^{13}$ or CN, a $C_3$-$C_6$ alkenyl radical, a cyclohexyl or benzyl radical, a phenyl radical optionally substituted with a chlorine atom or a linear or branched $C_1$-$C_{12}$ alkyl radical, or a 2-tetrahydropyranyl radical, $R^{15}$ and $R^{16}$ are identical or different and each represent a $C_1$-$C_4$ alkyl radical or a phenyl radical, $R^{17}$ represents a hydrogen atom, a $C_1$-$C_8$ alkyl radical or a phenyl radical, $R^{18}$ represents a radical —$CONH_2$, —$CONHR^{13}$, —$CON(R^{13})_2$, —$P(O)(OR^{13})_2$ or 2-pyridyl:

formula (V)

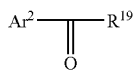

in which:

$Ar^2$ has the same meaning as $Ar^1$ of formula (IV) when n=1, $R^{19}$ represents a radical chosen from the group consisting of a radical $Ar^2$, a linear or branched $C_1$-$C_{12}$ alkyl radical, a $C_6$-$C_{12}$ cycloalkyl radical and a cycloalkyl radical forming a $C_6$-$C_{12}$ ring with the carbon of the ketone or a carbon of the radical $Ar^2$, these radicals possibly being substituted with one or more substituents chosen from the group consisting of —F, —Cl, —Br, —CN, —OH, —$CF_3$, —$OR^{13}$, —$SR^{13}$, —$COOR^{13}$, linear or branched $C_1$-$C_{12}$ alkyl radicals optionally bearing a group —OH, —$OR^{13}$ and/or —CN, and linear or branched $C_1$-$C_8$ alkenyl radicals;

formula (VI)

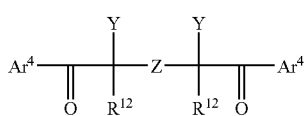

in which:

$R^{12}$, which may be identical or different, have the same meanings as in formula (IV), Y, which may be identical or different, represent X and/or $R^4$, Z represents:
a direct bond,
a $C_1$-$C_6$ divalent alkylene radical, or a phenylene, diphenylene or phenylene-T-phenylene radical (T: linear or branched $C_1$-$C_{12}$ alkyl), or alternatively forms, with the two substituents $R^{12}$ and the two carbon atoms bearing these substituents, a cyclopentane or cyclohexane nucleus, a divalent group —O—$R^{19}$—O—, —O—$SiR^{15}R^{16}$—O—$SiR^{15}R^{16}$—O—, or —O—$SiR^{15}R^{16}$—O—, $R^{20}$ represents a $C_2$-$C_8$ alkylene, $C_4$-$C_6$ alkenylene or xylylene radical, or alternatively the species:

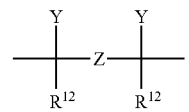

corresponds to —O—O— and $Ar^4$ has the same meaning as $Ar^1$ of formula (IV) when n=1.

the thioxanthone family of formula (VII):

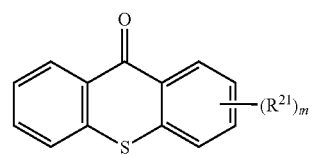

m=0 to 8, $R^{21}$, which may be identical or different substituents on the aromatic nucleus (nuclei), represent a linear or branched $C_1$-$C_{12}$ alkyl radical, a $C_6$-$C_{12}$ cycloalkyl radical, a radical $Ar^1$, a halogen atom or a group —OH, —$OR^{13}$, —CN, —$NO_2$, —$COOR^{13}$, —$OCOR^{13}$, —$N(R^{13})_2$, —O—$R^{13}$—$(NR^{13})_2$—CHO, —O-phenyl, —$CF_3$, —$SR^{13}$, —S-phenyl, —$SO_2$-phenyl, —O-alkenyl or —Si $(R^{13})_3$.

the xanthene family of formula (VIII):

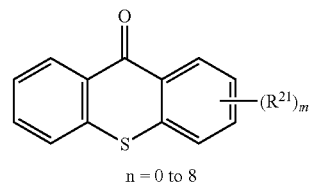

n = 0 to 8 the xanthone family of formula (IX):

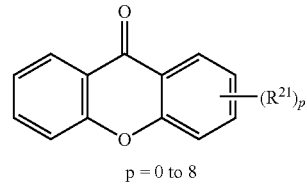

p = 0 to 8 the naphthalene family of formula (X):

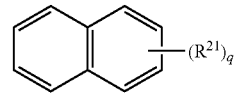

q = 0 to 8 the anthracene family of formula (XI):

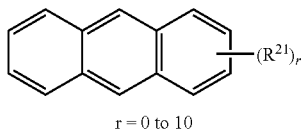

r = 0 to 10 the phenanthrene family of formula (XII):

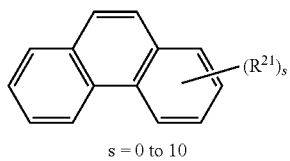

s = 0 to 10 the pyrene family of formula (XIII):

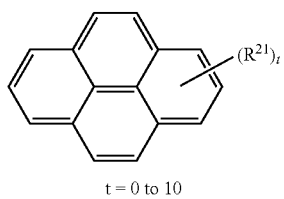

t = 0 to 10 the fluorene family of formula (XIV):

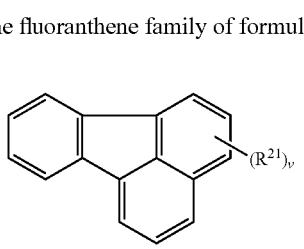

u = 0 to 9 the fluoranthene family of formula (XV):

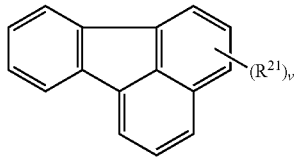

v = 0 to 10 the chrysene family of formula (XVI):

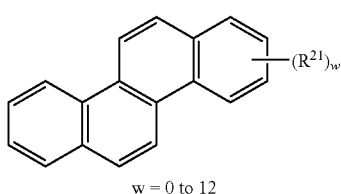

w = 0 to 12 the fluorone family of formula (XVII):

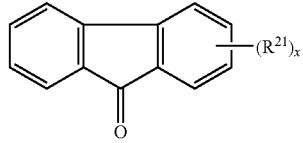

with x=0 to 8, for example 2,7-dinitro-9-fluorenone, the chromone family of formula (XVIII):

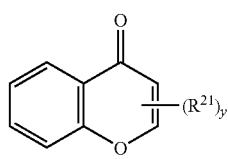

with y = 0 to 6 the eosin family of formula (XIX):

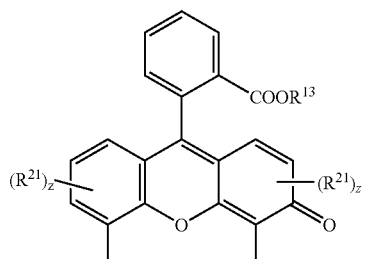

with z = 0 to 5

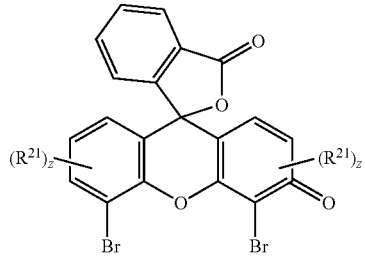

with z = 0 to 6 the erythrosin family of formula (XX):

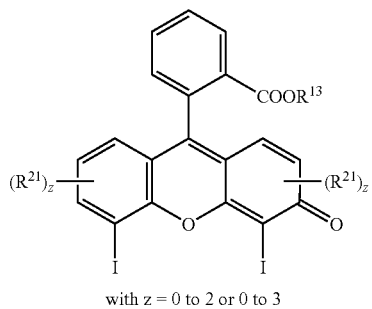

with z = 0 to 2 or 0 to 3 the erythrosin family of formula (XXI):

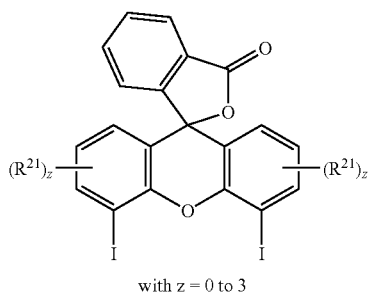

with z = 0 to 3 the biscoumarin family of formula (XXII):

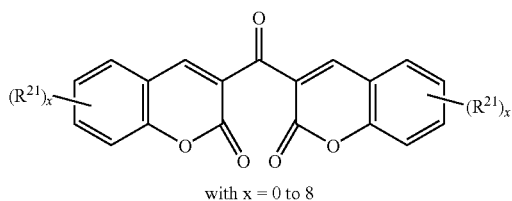

with x = 0 to 8 the thioxanthone family of formula (XXIII):

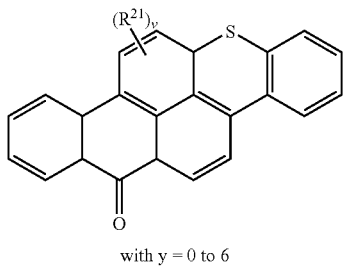

with y = 0 to 6 the thioxanthone family of formula (XXIV):

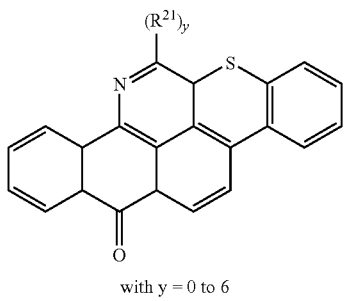

with y = 0 to 6

For formulae (VIII) to (XXIII), the group $R^{21}$ has the same definition as for the molecule (VII).

Other sensitizers may be used. It is especially possible to use the photosensitizers described in documents U.S. Pat. Nos. 4,939,069; 4,278,751; 4,147,552 and also the group consisting of the compounds of the coumarin, conjugated diketone, fluorone, amino ketone and para-aminostyryl ketone family, and also mixtures thereof.

According to one preferred mode, the photosensitizer (E) is chosen from the group consisting of compounds of the anthracene, thioxanthone, camphorquinone and phenanthrenequinone class, and also mixtures thereof.

According to another preferred mode, the dental composition comprises as photosensitizer (E) a salt of a thioxanthone substituted with at least one group comprising an ammonium function. The use of this type of photosensitizer has the advantage of avoiding spurious colorations when the dental composition is crosslinked for the manufacture of a dental prosthesis.

According to a first variant of the invention, the associated anion of the salt of the thioxanthone substituted with at least one group comprising an ammonium function is chosen from the following anions:

a halide, $BF_4^-$, $PF_6^-$; $SbF_6^-$; the anion (III) of formula $[BX_aR_b]^-$ as defined above, $R_fSO_3^-$; $(R_fSO_2)_3C^-$ or $(R_fSO_2)_2N^-$ with $R_f$ being a linear or branched alkyl radical substituted with at least one halogen atom, preferably a fluorine atom.

According to a second variant of the invention, the photosensitizer (E), optionally in combination with at least one camphorquinone, a phenanthrenequinone and/or a substituted anthracene, has the formula:

(XXV)

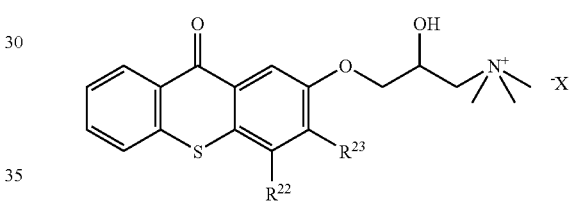

in which formula:

$R^{22}$ and $R^{23}$ are identical or different and represent a hydrogen or an optionally substituted $C_1$-$C_{10}$ alkyl radical, and preferably R22=R23=methyl, ($X^-$) being an anionic species, preferably a halide; $BF_4^-$, $PF_6^-$; $SbF_6^-$; the anion (III) of formula $[BX_aR_b]^-$ defined as above, $R_fSO_3^-$; $(R_fSO_2)_3C^-$ or $(R_fSO_2)_2N^-$, with $R_f$ being a linear or branched alkyl radical substituted with at least one halogen atom, preferably a fluorine atom, and even more preferably ($X^-$) is chosen from the borates having the following formulae: $[B(C_6H_3(CF_3)_2)_4]^-$ and $[B(C_6F_5)_4]^-$.

According to one preferred mode, the photosensitizer (E), optionally in combination with at least one camphorquinone, a phenanthrenequinone and/or a substituted anthracene, has the formula:

(PS-31)

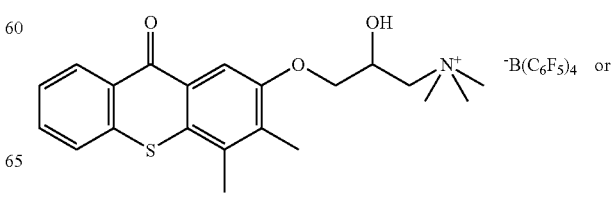

-continued (PS-32)

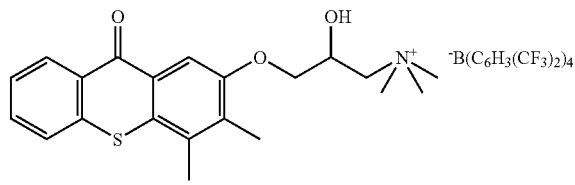

(PS-50)

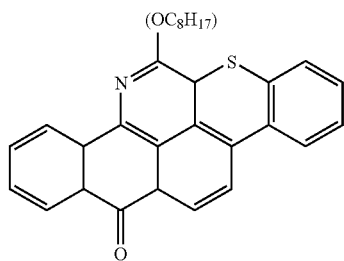

In the context of the present invention, the photosensitizers have a residual absorption of UV light of between 200 and 500 nm and preferably 400 to 500 nm for the preparation of dental prostheses. For dental restoration, a photosensitizer with a residual absorption of UV light of above 400 nm will be preferred.

According to one preferred variant, the photosensitizers will be chosen from those of the families (VII), (X), (XI), (XIII), (XXIII), (XXIV) and (XXV). According to another embodiment, the photosensitizer is chosen from the group consisting of the following compounds:

(PS-30): 3-(3,4-dimethyl-9-oxo-9-thioxanthenen-2-yloxy)-2-hydroxypropyl)trimethylammonium chloride;

(PS-31): 3-(3,4-dimethyl-9-oxo-9-thioxanthenen-2-yloxy)-2-hydroxypropyl)trimethylammonium tetrakis(pentafluorophenyl)borate;

(PS-32): 3-(3,4-dimethyl-9-oxo-9-thioxanthenen-2-yloxy)-2-hydroxypropyl)trimethylammonium tetrakis(bis(trifluoromethyl)phenyl)borate;

(PS-33): phenanthrenequinone;
(PS-34): camphorquinone;
(PS-35): acenaphthenequinone;
(PS-36): dibenzoyl peroxide;
(PS-37): 2-ethyl-9,10-dimethoxyanthracene;
(PS-38): 9,10-diethoxyanthracene;
(PS-39): 9,10-dibutoxyanthracene;
(PS-40): 9-hydroxymethylanthracene;
(PS-41): 2-dimethylaminothioxanthone;
(PS-42): 3-ethylcarboxy-7-methoxythioxanthone;
(PS-43): 1-phenylthio-4-propoxythioxanthone;
(PS-44): 2-methoxythioxanthone;
(PS-45): 2-(N,N-diethylaminopropoxy)thioxanthone;
(PS-46): 2-isopropylthioxanthone;
(PS-47): 1-chloro-4-propoxythioxanthone;
(PS-48): 4-isopropylthioxanthone;

(PS-49)

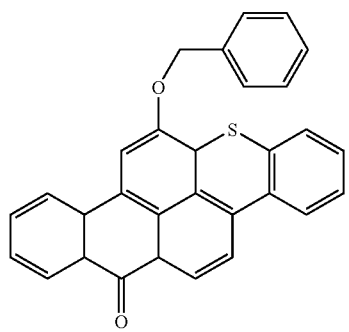

and mixtures thereof.

In the context of the invention, the stability on storage, the mechanical strength, the modulus of elasticity and the compression strength of the material obtained after crosslinking are markedly improved. When the thioxanthones of the family described by formula (XXV) are used, an additional advantage is observed in using the thioxanthones (PS-31) or (PS-32), optionally in combination with at least one camphorquinone, a phenanthrenequinone and/or a substituted anthracene, namely the absence of residual coloration.

Besides the reinforcing fillers, pigments may be used to color the dental composition according to the envisioned use and the ethnic groups.

For example, red pigments in the presence of microfibers are used for dental compositions used for the preparation of dental prostheses in order to simulate the blood vessels.

Pigments based on metal oxides (iron oxide and/or titanium oxide and/or aluminum oxide and/or zirconium oxide, etc.) are also used for the dental compositions used for the preparation of restoration material, in order to obtain a crosslinked material of ivory color.

Other additives may be incorporated into the dental compositions according to the invention. For example, biocides, stabilizers, flavor agents, plasticizers and adhesion promoters.

Among the additives that may be envisioned, crosslinkable and/or polymerizable coreagents of organic type will advantageously be used. These coreagents are liquid at room temperature or thermofusible at a temperature below 100° C., and each coreagent comprises at least two reactive functions such as oxetane-alkoxy, oxetane-hydroxyl, oxetane-alkoxysilyl, carboxy-oxetane, oxetane-oxetane, alkenyl ether-hydroxyl, alkenyl ether-alkoxysilyl, epoxy-alkoxy, epoxy-alkoxysilyl, dioxolane-dioxolane-alcohol, etc. Examples that may be mentioned include the resins R70 and R71.

The dental compositions according to the invention may be used for numerous dental applications, and in particular in the field of dental prostheses, in the field of dental restoration and in the field of temporary teeth.

The dental composition according to the invention is preferably in the form of a single product containing the various components ("monocomponent"), which facilitates its implementation, especially in the field of dental prostheses. Optionally, the stability of this product may be ensured by organic derivatives containing amine functions according to the teaching of document WO 98/07798.

In the field of dental prostheses, the product in the "monocomponent" form may be deposited using a syringe directly onto the plaster model or into a key. Next, it is polymerized (polymerization by possible successive layers) using a UV lamp (visible light spectrum 400 to 500 nm).

In general, it is possible to make a durable and esthetic dental prosthesis in 10 to 15 minutes.

It should be noted that the products obtained using the dental composition according to the invention are non-porous. Thus, after optional polishing using a felt brush, for example, the surface of the dental prostheses obtained is smooth and shiny and it is therefore unnecessary to use varnish.

The applications in the field of dental prostheses are essentially those of the removable prosthesis, which may be divided into two types:

total prosthesis in the case of a patient who has had all his teeth removed;

partial prosthesis due to the absence of several teeth, reflected either by a temporary prosthesis or a skeleton denture.

In the field of dental restoration, the dental composition according to the invention may be used as material for stopping the front and back teeth in different shades (for example "VITA" shades), which is quick and easy to use.

Since the dental composition is nontoxic and polymerizable in thick layers, it is not essential to polymerize the material in successive layers. In general, a single injection of the dental composition is sufficient.

The preparations for dental prostheses and for restoration materials are made according to the usual techniques of the art.

In the case of application of the dental composition to a tooth, either the tooth may be pretreated with an acid etch and then with an attachment primer, which may itself be photo-crosslinkable, or the dental composition may be prepared as a mixture with an attachment primer before its use.

The invention also relates to a process for treating a reinforcing filler, in particular a dental reinforcing filler, characterized in that the filler is treated:

a) with at least one organosilicon coupling agent (F), and
b) with at least one compound (G), said organosilicon coupling agent (F) comprising at least one reactive function (rfA) directly linked to a silicon atom reacting with the dental filler, and at least one reactive function (rfB) not directly linked to a silicon atom reacting with a reactive function (rfC) of the compound (G).

According to one preferred mode of the process according to the invention:

the reactive function (rfA) directly linked to a silicon atom of the organosilicon coupling agent (F) is an alkoxy, enoxy and/or hydroxyl function;

the reactive function (rfB) not directly linked to a silicon atom of the organosilicon coupling agent (F) is an oxirane, oxetane, hydroxyl, acid, carboxylic acid anhydride or diol function; and the reactive function (rfC) of the compound (G) is an oxirane, oxetane, alkenyl ether or carbonate function.

According to another embodiment, the filler is treated:

a) with at least one organosilicon coupling agent (F) comprising at least one alkoxy and/or hydroxyl function directly linked to a silicon atom and to at least one oxirane, oxetane, hydroxyl and/or diol function; and b) with at least one compound (G) comprising at least one oxirane, oxetane, alkenyl ether and/or carbonate function.

The process according to the invention is particularly suitable for treating a dental filler. This process (I) comprises the following steps:

a) the dental filler (B) and at least one organosilicon coupling agent (F) comprising at least one alkoxy and/or hydroxyl function directly linked to a silicon atom and to at least one oxirane, oxetane, hydroxyl and/or diol function, are mixed together in solvent medium, b) the solvent is evaporated off to obtain an intermediate dental filler (B-1), c) the intermediate dental filler (B-1) is subjected to a heat treatment so as to allow the coupling reaction between the intermediate dental filler (B-1) and the coupling agent (F) and thus to obtain an intermediate dental filler (B-2), d) the intermediate dental filler (B-2) is then mixed in solvent medium with at least one compound (G) comprising at least one oxirane, oxetane, alkenyl ether and/or carbonate function, e) the solvent is evaporated off to obtain an intermediate dental filler (B-3), and f) the intermediate dental filler (B-3) is subjected to a heat treatment so as to allow the reaction between the intermediate dental filler (B-3) and compound (G) and thus to obtain a treated dental filler (B-4).

According to one preferred mode, the heat treatment of steps c) and f) of the process (I) is performed by heating to a temperature of less than or equal to 200° C., preferably less than or equal to 160° C. and even more preferably of between 100° C. and 165° C.

The organosilicon coupling agent (F), the compound (G) and the dental reinforcing filler (B) are as defined in the dental composition according to the invention.

The invention also relates to a reinforcing filler obtained via the process according to the invention.

The Examples and Tests below are given for illustrative purposes. They especially allow the invention to be understood more clearly and allow some of its advantages to be brought out and illustrate some of its implementation variants.

Examples and Tests

Structures

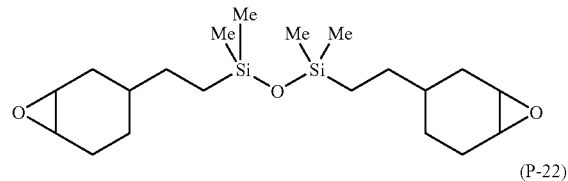

(S-1)

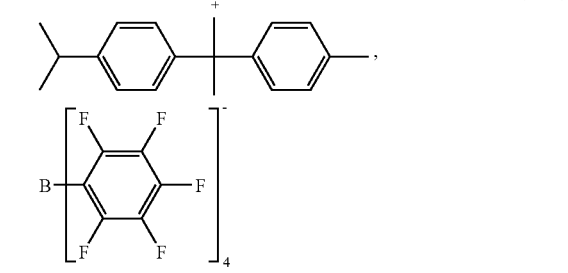

(P-22)

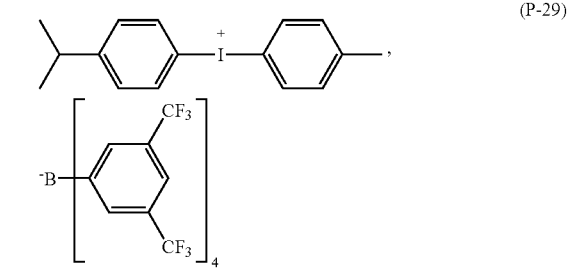

(P-29)

-continued (PS-31)

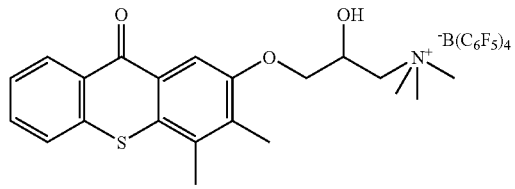

resin sold by the company Dow Chemical under the reference ERLX-4360 (resin of the family described under the structure S-104 mentioned above), filler (B-1): quartz glass (particle size=1.5 μm, $SiO_2$ 56%; SrO 14%; $B_2O_3$ 14%; $Al_2O_3$ 14%; F 2%) sold by the company Schott under the reference G018-163 filler (B-2): quartz glass (particle size=1.5 μm, $SiO_2$ 55%; BaO 25%; $B_2O_3$ 10%; $Al_2O_3$ 10%) sold by the company Schott under the reference GM27-884.

Preparation of a Thioxanthone Containing Ammonium Borate Functionality (S-61):

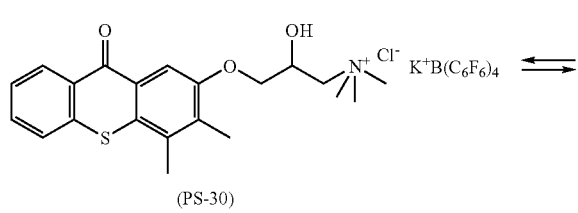 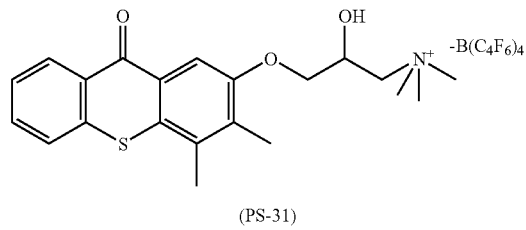

(PS-30) (PS-31)

1.02 g of 3-(3,4-dimethyl-9-oxo-9H-thioxanthen-2-yloxy)-2-hydroxypropyl)trimethylammonium chloride (sold by the company Aldrich); 2.688 g of "Kisbore" salt $KB(C_6F_5)_4$ (prepared by the company Rhodia) and 50 ml of isopropanol are introduced, protected from light, into an opaque flask and the mixture is left under magnetic stirring for 48 hours at room temperature. The mixture is then poured into demineralized water (200 ml). A yellow precipitate forms. The suspension is filtered through a Büchner funnel and the solid is dried for 24 hours in an oven at 100° C. The salt referenced (PS-31) is obtained (melting point 235° C.; absorption maximum λmax=397.3 nm).

EXAMPLE 1

Comparative

Treatment of the Filler (B-1)

a) Treatment of the Filler with a Coupling Agent Containing Diol Functionality (F-2):

The silane glycidyloxypropyltrimethoxysilane or GLYMO

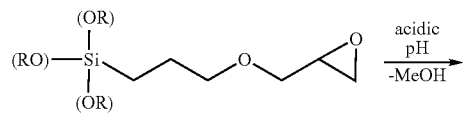

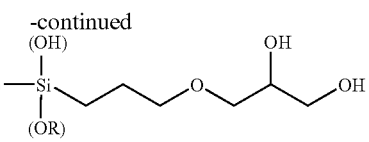

of formula (F-1) sold by the company Degussa is hydrolyzed in acidic medium according to the following reaction:

with R=methyl

The compound (F-2) is in a more or less polycondensed form and is soluble in aqueous phase.

The solution used is a solution containing 40% silane (F-2) with a pH=3-4.

12.5 g of this 40% solution of silane (F-2) are poured into a beaker and made up with 200 g of demineralized water. 200 g of filler (B-1) are poured into this solution and the mixture is stirred for 1 hour at room temperature using an impeller stirrer. The mixture is poured into a crystallizing dish and the filler is dried in an oven for 16 hours at 150° C. The filler is then screened through a 250 micron gauze.

b) Treatment with a Coupling Agent Containing Oxirane Functionality

For comparative purposes, we performed the hydrolysis of the silane glycidyloxypropyltrimethoxysilane in neutral medium and we removed the majority of the methanol arising from the hydrolysis reaction by distillation. Analysis by $^1$H NMR reveals that the epoxide function is not hydrolyzed when this solution is cold-stored for several weeks.

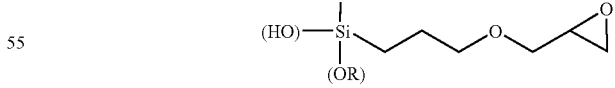

A 40% solution of silane (F-3) at pH=7 is used.

12.5 g of this 40% solution are poured into a beaker and made up with 200 g of demineralized water. 200 g of untreated filler (B-1) are poured into this solution and the mixture is stirred for 1 hour at room temperature using an impeller stirrer. The mixture is poured into a crystallizing dish and the filler is dried in an oven for 16 hours at 150° C. The filler is then screened through a 250 micron gauze.

c) Properties of the Dental Compositions 11.625 g of siloxane resin containing an oxirane function (S-1) are placed in a centrifugal mixer (Hauschild brand).

1.125 g of a 4% solution of dispersant (C-1) (sold by the company Byk under the reference Disperbyk-164®) are added. The mixture is stirred for 16 seconds using the centrifugal mixer at 3000 rpm, and 3 g of ytterbium trifluoride are added. The mixture is stirred for a further 16 seconds with the centrifugal mixer at 3000 rpm, and 1.25 g of photoinitiator system (P) containing 30% by weight of photoinitiator (P-22) and 0.89% by weight of the photosensitizer of formula (PS-31) as a solution in (S-1) are then added.

The mixture is stirred for 16 seconds with the centrifugal mixer at 3000 rpm, at room temperature, and 25 g of the filler (B-1) are then added:
untreated (formulation 1t),
or treated according to a) (formulation 1a);
or treated according to b) (formulation 1b).

The mixture is stirred for 16 seconds with the centrifugal mixer. 3 grams of a filler of combustion silica type (B-3) ($SiO_2$>99%, sold by the company Degussa under the reference OX50®) are added and the mixture is then stirred for 16 seconds. Finally, 5 g of a filler of combustion silica type (B-4) sold by the company Degussa under the reference R202® are finally added, and the mixture is then stirred for 16 seconds.

The change in viscosity over time is monitored for the three formulations. The moment at which the formulation of the composite is gelled and is no longer manipulable is noted. The results are given in Table 1.

TABLE 1

| Comparative | Stability at 25° C. |
| --- | --- |
| Formulation 1t | <24 h |
| Formulation 1a | <24 h |
| Formulation 1b | 48 h |

Example 2

Invention a) Treatment with the Resin Containing an Oxirane Function (S-1) of the Fillers Obtained in Example 1a)

A solution containing 2.5% by weight of resin containing an oxirane function (S-1) is prepared in acetone.

100 g of filler (B-1) treated according to Example 1a) are poured onto 100 g of this 2.5% solution and stirred mechanically at room temperature for about one minute. The mixture is then poured into a crystallizing dish and the acetone is evaporated off at room temperature.

The residue is heated at 150° C. for 16 hours in order to polymerize the resin containing an oxirane function (S-1) at the surface of the filler. The filler is then screened to obtain a powder.

b) Treatment with the Resin Containing an Oxirane Function (S-1) of the Fillers Obtained in Example 1b)

A solution containing 2.5% by weight of resin containing an oxirane function (S-1) is prepared in acetone.

100 g of filler (B-1) treated according to Example 1b) are poured onto 100 g of this 2.5% solution and stirred mechanically at room temperature for about one minute. The mixture is then poured into a crystallizing dish and the acetone is evaporated off at room temperature. The residue is heated at 150° C. for 16 hours in order to polymerize the resin containing an oxirane function (S-1) at the surface of the filler. The filler is then screened to obtain a powder.

c) Properties of the Dental Compositions

The two fillers of Examples 2-a) and 2-b) are formulated in the same way as in Example 1-c), the overall filler content is 72% by weight relative to the weight of the composition, to obtain two dental compositions (formulations (2a) and (3b), respectively), the stability and the change over time of which are monitored.

TABLE 2

| Invention | Treatment | Stability at 25° C. |
| --- | --- | --- |
| Formulation (2a) | a) solution containing 2.5% by weight of resin (S-1) | 1 month |
| Formulation (2b) | b) solution containing 2.5% by weight of resin (S-1) | 1 week |

Comparison of the results between:
formulations (1a) and (2a), and
formulations (1b) and (2b) shows a marked improvement in stability.

Example 3

Invention, Double Treatment of the Filler

Variation of the Content of Resin Containing an Oxirane Function (S-1)

Example 2a) is repeated, varying the content of resin containing an oxirane function (S-1) during the treatment of the filler (B-1).

A dental composition is then formulated as in Example 2c).

The exact composition corresponds to the following formulation (the overall filler content is 66% by weight relative to the weight of the composition):

| | |
| --- | --- |
| resin containing an oxirane function (S-1) | 29.25 g |
| dispersant solution containing 4% (C-1) | 2.25 g |
| photoinitiator system (P) (see Example 1): (P-22) + (PS-31) | 2.5 g |
| ytterbium trifluoride | 6 g |
| double-treated filler (B-1) | 50 g |
| untreated filler (B-3) combustion silica OX50 ® | 5 g |
| untreated filler (B-4) combustion silica R202 ® | 5 g |

The change in the epoxy content is monitored by potentiometric assay in solution of the composite in the perchloric acid assay solution.

TABLE 3

| Dental compositions | % by weight of the resin (S-1) in acetone for the treatment of the filler (B-1): | Degree of conversion of the epoxy % after 26 days | Stability at 25° C. (months) |
| --- | --- | --- | --- |
| Control formulation (1t) | 0 | not measurable | 0 |
| Formulation (3a) | 1 | 23 | 1 |

TABLE 3-continued

| Dental compositions | % by weight of the resin (S-1) in acetone for the treatment of the filler (B-1): | Degree of conversion of the epoxy % after 26 days | Stability at 25° C. (months) |
|---|---|---|---|
| Formulation (3b) | 2.5 | 19 | 3 |
| Formulation (3c) | 5 | 16 | >12 months |

Example 4

Invention, Double Treatment of the Filler
Preparation of a Dental Composition with an Overall Filler Content of 70% by Weight Relative to the Weight of the Composition 11.5 g of siloxane resin containing an oxirane function (S-1) are placed in a Hauschild centrifugal mixer. 2.25 g of a 4% solution of dispersant (C-1) sold by the company Byk under the reference Disperbyk-164® are added. The mixture is stirred for 16 seconds with the centrifugal mixer at 3000 rpm, and 3 g of ytterbium trifluoride are added. The mixture is stirred for a further 16 seconds with the centrifugal mixer at 3000 rpm, and 1.25 g of a photoinitiator system (P) containing 30% by weight of photoinitiator (P-22) and 0.89% by weight of photosensitizer based on (PS-31) are then added to the resin (S-1). The mixture is stirred for 16 seconds with the centrifugal mixer at 3000 rpm and at room temperature, and 27 g of the filler (B-1) treated according to Example 2a) and then according to Example 3 (treatment of the filler (B-1) with a solution containing 5% by weight of the resin (S-1) in acetone) are then added. The mixture is stirred for 16 seconds with the centrifugal mixer. 2.5 g of combustion silica (B-3) (sold by the company Degussa under the reference OX50®, $SiO_2$>99%) treated as for the filler (B-1) are added and the mixture is then stirred for 16 seconds. Finally, 2.5 g of combustion silica (B-4) (sold by the company Degussa under the reference R202®) are added and the mixture is stirred for 16 seconds.

The change in viscosity over time is monitored for the formulation with treated fillers. This formulation is stable for more than 1 year at 25° C.

Samples as described in standard ISO 4049 are crosslinked using a halogen lamp of Demetron Optilux 500 type (irradiation time: 2 times 40 seconds).

The flexural strength measured according to standard ISO-4049 is 90 Mpa+/−10 with a bending modulus of 9000 MPa.

The depth of crosslinking is 4 mm after irradiation for 40 seconds.

The volume shrinkage calculated from the densities measured before and after polymerization is: −1.6%+/−0.2.

The exact composition corresponds to the following formulation (the overall filler content is 70% by weight relative to the weight of the composition):

| | |
|---|---|
| resin containing an oxirane function (S-1) | 11.5 g |
| dispersant solution (C-1) | 2.25 g |
| photoinitiator system (P): (P-22) + (PS-31) | 1.25 g |
| treated ytterbium trifluoride | 3 g |
| double-treated filler (B-1) | 27 g |
| untreated filler (B-3) combustion silica OX50 ® | 2.5 g |
| untreated filler (B-4) combustion silica R202 ® | 2.5 g |

Example 5

Invention, Double Treatment of the Filler

The impact of the nature of the photosensitizers on the coloration of the composition after irradiation with a dentistry lamp was compared. Example 4 was reproduced, modifying the nature and amount of photosensitizer introduced into the composition.

The dental compositions described in Examples 2 to 5 are crosslinked to a thickness of 2 to 3 mm with an irradiation time of between 30 seconds and 1 minute using an Optilux Demetron lamp. The values L*,a*,b* are measured using a Minolta CR200 chromameter or calorimeter, after 15 minutes of crosslinking on a white background and after 5 days of crosslinking.

The chromatic difference obtained Δc defined such that $\Delta c=[(\Delta a)^2+(\Delta b)^2]^{1/2}$, is deduced therefrom.

It is found that the crosslinking with a Demetron Optilux 500 dentistry lamp of the dental compositions formulated with the photosensitizer (PS-31), alone or in combination with other photosensitizers, for example (PS-39); (PS-34) and (PS-33), does not give rise to any coloration defect (no phenomenon of reddening during irradiation with a chromatic value a>1 immediately after irradiation).

TABLE 4

| Example | Photosensitizer(s) | Concentration(s) ppm | T = 15 minutes; L, a, b | | | T = 5 days; L, a, b | | | Δc |
|---|---|---|---|---|---|---|---|---|---|
| | | | L* | a* | b* | L* | a* | b* | |
| 5-a | PS-47 | 67 | 69.15 | 2.87 | 7.68 | 73.4 | −0.5 | 9.55 | 3.85 |
| 5-b | PS-30 | 220 | 71.1 | 1.70 | 16.2 | 75.85 | −1.51 | 14.75 | 3.5 |
| 5-c | PS-31 | 220 | 76.35 | 0.29 | 12.4 | 78.06 | −0.63 | 11.9 | 1.08 |
| 5-d | PS-31 | 170 | 72.8 | 1.01 | 10.02 | 75.24 | −0.4 | 8.73 | 1.51 |
| 5-e | PS-31; PS-39 | 170; 130 | 73.4 | 0.46 | 14.16 | 76.47 | −1.0 | 13.04 | 1.84 |
| 5-f | PS-31; PS-34; PS-39 | 170; 100; 120 | 70.1 | −0.21 | 15.68 | 73.69 | −1.33 | 13.94 | 2.07 |
| 5-g | PS-31; PS-33; PS-39 | 170; 50; 110 | 69.08 | 1.41 | 15.58 | 73.42 | −0.79 | 15.07 | 2.26 |
| 5-h | PS-34; PS-39 | 100; 160 | Kinetics insufficient for crosslinking in 1 minute to 3 mm | | | | | | |

The use of the combination of thioxanthone (PS-31) makes it possible to eliminate the coloration problems, but also the kinetic problems encountered by using camphorquinone (PS-34) alone or camphorquinone in combination with the anthracene derivative (PS-39) in low concentration (of less than 0.1% in the case of Example 5-h).

Example 6

Invention, Double Treatment of the Filler

Example 5 is repeated, replacing:
the photoinitiator (P-22) with the photoinitiator (P-29); and
the photoinitiator system (P) with the photoinitiator system (P') containing 30% by weight of photoinitiator (P-29) and 0.89% by weight of photosensitizer based on (PS-31) in the resin (S-1).

Chromatic Difference:
after 15 minutes of crosslinking on a white background, $L^*, a^*, b^* = 72.1; +0.10; 9.53$ respectively; and
after 5 days, $L^*, a^*, b^* = 75; -0.25; 8.1$, respectively.
$=> \Delta c = [(\Delta a)^2 + (\Delta b)^2]^{1/2} = 1.47$.

Example 7

Invention, Double Treatment of the Filler a) Treatment of the Filler (B-2) with Glycidyloxypropyltrimethoxysilane 300 g of an acetone solution containing 2.5% of glycidyloxypropyltrimethoxysilane are introduced under nitrogen onto 300 g of glass B-2. The mixture is then stirred vigorously using a Teflon-coated impeller for 8 hours at room temperature. The "slurry" is then filtered to recover the glass and the filter cake is screened through a 200-micron gauze. The screened glass is air-dried at 110° C. for 8 hours.

b) Treatment of the Filler (B-2) Obtained from Example 7-a) with the Mixture of Resins (S-1) and (S-104) Containing Oxirane Functionality.

300 g of a solution in acetone containing 3.8% of (S-1) and 3.8% of (S-104) are introduced onto 300 g of glass treated according to Example 7-a) and the mixture is then stirred under nitrogen using a Teflon-coated impeller for 8 hours at room temperature.

The glass is filtered through a polyamide filter and then screened through a 200-micron gauze and finally dried at 110° C. for 12 hours.

The treated glass obtained (double-treated filler) is then used to make the following dental composition (the overall filler content is 75% relative to the total weight of the composition):

| | |
|---|---|
| resin containing an oxirane function (S-1) | 4.5 g |
| resin containing oxirane functionality (S-104) | 4.5 g |
| dispersant solution (C-1) | 2.25 g |
| photoinitiator system (P): (P22) + (PS-31) | 1.25 g |
| double-treated filler [B-2] | 32.5 g |
| double-treated filler (B-3), combustion silica OX50 ® | 2.5 g |
| untreated filler (B-4), combustion silica R202 ® | 2.5 g |

The change in the epoxy content over time of the composition is monitored. It is observed that the composition is stable for at least 9 months at 25° C. with a degree of conversion of the epoxys of less than 20%.

Samples as described in standard ISO 4049 are crosslinked using a Demetron Optilux 500 halogen lamp (irradiation time: 2 times 40 seconds).

The bending strength measured according to standard ISO-4049 is 90 Mpa+/−10 with a bending modulus of 800 MPa+/−1000.

The depth of crosslinking is 4 mm after irradiation for 40 seconds.

The volume shrinkage calculated from the densities measured before and after polymerization is −1.4%+/−0.2.

Example 8

Invention, Double Treatment of the Filler

The treated glass (double-treated filler) obtained according to Example 7b) is then used to make the following dental composition (the overall filler content is 75% relative to the total weight of the composition):
resin containing an oxirane function (S-1) 4.5 g

| | |
|---|---|
| resin containing an oxirane function (S-1) | 4.5 g |
| resin containing oxirane functionality (S-104) | 4.5 g |
| dispersant solution (C-1) | 2.25 g |
| photoinitiator system (P): (P22) + (PS-31) | 1.25 g |
| double-treated filler [B-2] | 32.5 g |
| double-treated filler (B-3), combustion silica OX50 ® | 2.5 g |
| untreated filler (B-5), colloidal silica as a solution at a concentration of about 40% by weight in a resin (S-96) sold by the company Hanse Chemie | 2.5 g |

The change in the epoxy content over time of the composition is monitored. It is observed that the composition is stable for at least 9 months at 25° C. with a degree of conversion of the epoxys of less than 20%.

Samples as described in standard ISO 4049 are crosslinked using a Demetron Optilux 500 halogen lamp (irradiation time: 2 times 40 seconds).

The bending strength measured according to standard ISO-4049 is 100 MPa+/−10 with a bending modulus of 8000 MPa+/−1000.

The depth of crosslinking is 4 mm after irradiation for 40 seconds.

The volume shrinkage calculated from the densities measured before and after polymerization is −1.4+/−0.2.

The invention claimed is:
1. A dental composition comprising:
   (1) at least one cationically reactive compound (A);
   (2) at least one dental filler (B);
   (3) optionally at least one dispersant (C) comprising at least one organic polymer or copolymer;
   (4) at least one cationic photoinitiator (D);
   (5) and optionally at least one photosensitizer (E),
where said composition comprising at least one dental filler (B) having been treated via a process (I) comprising the following steps:
   a) mixing in a solvent medium the at least one dental filler (B) with at least one organosilicon coupling agent (F) of the formula:

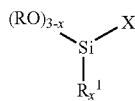
(F)

in which formula:

R is a hydrogen or a linear or branched $C_1$-$C_4$ alkyl radical, $R^1$ is a linear or branched alkyl radical or a phenyl radical, x is equal to 0, 1 or 2, and X is defined by one of the following formulae:

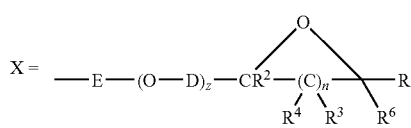
(M-1)

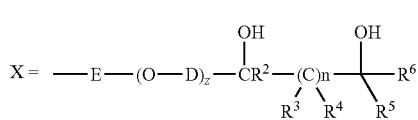
(M-2)

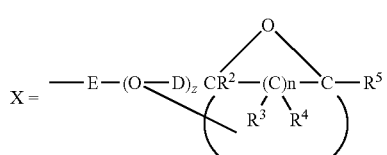
(M-3)

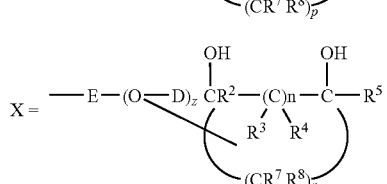
(M-4)

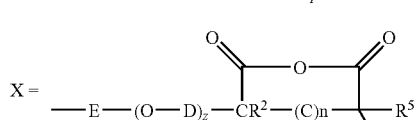
(M-5)

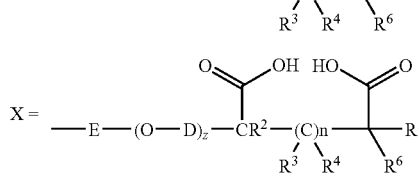
(M-6)

where:

E and D which are identical or different radicals chosen from linear or branched $C_{12}$-$C_{12}$ alkylene, z is equal to 0 or 1;

n is equal to 0 or 1;

p is equal to 0, 1, 2, 3, 4, 5 or 6;

$R^2$, $R^3$, $R^4$, $R^5$, $R^6$, $R^7$ and $R^8$ are radicals, which may be identical or different, representing a hydrogen or a linear or branched $C_1$-$C_{12}$ alkyl;

b) evaporating the solvent to obtain an intermediate dental filler (B-1), c) heat treating the intermediate dental filler (B-1) to allow the coupling reaction between the intermediate dental filler (B-1) and the coupling agent (F) and thus obtain an intermediate dental filler (B-2), d) mixing the intermediate dental filler (B-2) in a solvent medium with at least one compound (G) comprising at least one oxirane, oxetane, alkenyl ether and/or carbonate function, e) evaporating the solvent to obtain an intermediate dental filler (B-3), and f) heat treating the intermediate dental filler (B-3) to allow the reaction between the intermediate dental filler (B-3) and the compound (G) and thus to obtain a treated dental filler (B-4).

2. The dental composition as claimed in claim 1, in which the heat treating of the intermediate dental filler (B-1) and (B-3) in steps c) and f) of the process (I) is performed by heating the intermediate dental filler (B-1) and (B-3) to a temperature of less than or equal to 200° C.

3. The dental composition as claimed in claim 1, in which the overall content of dental fillers (B) represents up to 85% by weight relative to the total weight of the dental composition.

4. The dental composition as claimed in claim 1, in which the treatment of the dental filler (B) is performed with up to 20% by weight of the compound (G) and/or up to 20% by weight of the compound (F) relative to the total weight of the dental composition.

5. The dental composition as claimed in claim 1, in which the organosilicon coupling agent (F) is selected from the group consisting of the following compounds: glycidyloxypropyltrimethoxysilane, the product of hydrolysis of glycidyloxypropyltrimethoxysilane; glycidyloxypropyltriethoxysilane, the product of hydrolysis in acidic medium of glycidyloxypropyltriethoxysilane; glycidyloxypropyldimethoxymethylsilane and its hydrolysis product, β-(3,4-epoxycyclohexyl)ethyltriethoxysilane and its hydrolysis product, and β-(3,4-epoxycyclohexyl)ethyltrimethoxysilane and its hydrolysis product.

6. The dental composition as claimed in claim 1, in which the compound (G) is an organic or organosiloxane monomer, oligomer or polymer comprising at least one oxirane, oxetane, alkenyl ether and/or carbonate function.

7. The dental composition as claimed in claim 6, in which the compound (G) comprises at least one function selected from the group consisting of the structures (M-7) to (M-12) below:

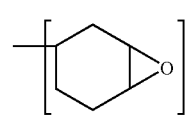
(M-7)

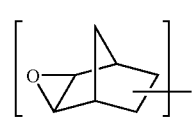
(M-8)

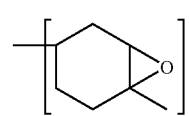
(M-9)

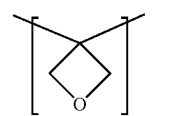
(M-10)

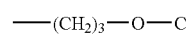
—(CH$_2$)$_3$—O—CH=CH$_2$;
(M-11)

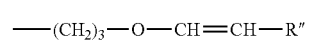
—(CH$_2$)$_3$—O—CH=CH—R″
(M-12)

with R″ representing a linear or branched $C_1$-$C_6$ alkyl radical.

8. The dental composition as claimed in claim 6, in which the compound (G) is a silicone oligomer (G-1) or a silicone polymer (G-2).

9. The dental composition as claimed in claim 8, in which the silicone polymer (G-2) or the silicone oligomer (G-1) is combined with a resin of formula (S-103) or (S-104):

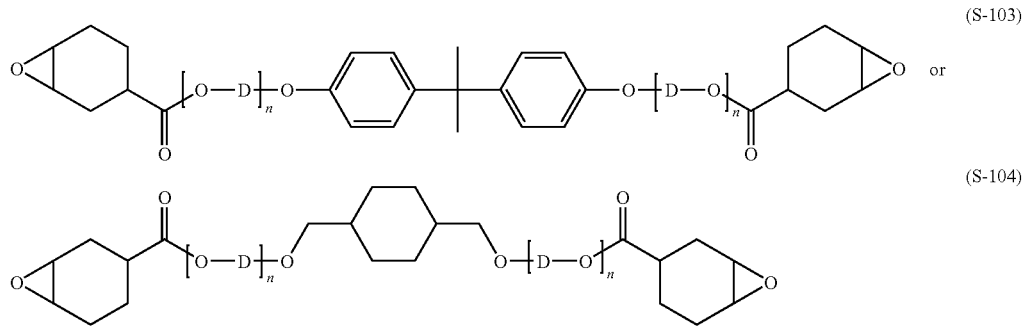

with:

$0 \leq n \leq 100$ and

D=radical chosen from linear or branched $C_1$-$C_{12}$ alkyls.

10. The dental composition as claimed in claim 8, in which the silicone oligomer (G-1) and the silicone polymer (G-2) comprise:

a) at least one unit of formula:

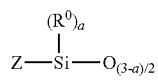
(M-13)

in which formula:

a=0, 1 or 2, $R^0$, which may be identical or different; represents an alkyl, cycloalkyl, aryl, vinyl, hydrogeno or alkoxy radical, Z, which may be identical or different, is an organic substituent comprising at least one oxirane, alkenyl ether, oxetane and/or carbonate function, and b) at least two silicon atoms.

11. The dental composition as claimed in claim 10, in which the silicone oligomer (G-1) and the silicone polymer (G-2) are selected from the group consisting of the compounds of formulae:

a)

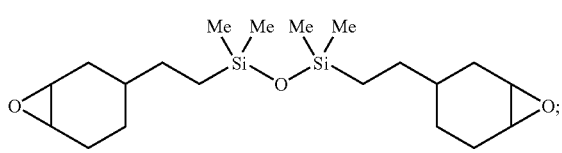
(S-1)

b)

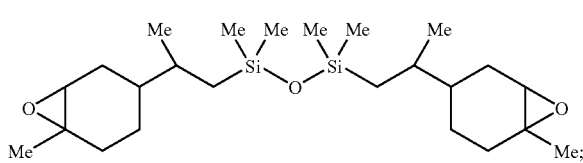
(S-2)

c)

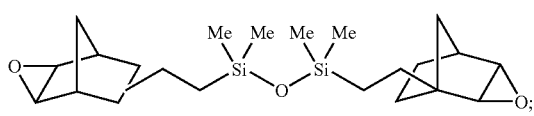
(S-3)

d)
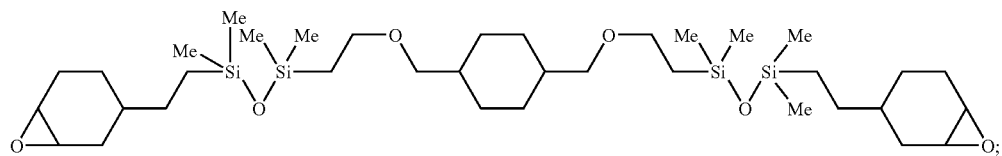
(S-4)
e)
(S-5)
f)
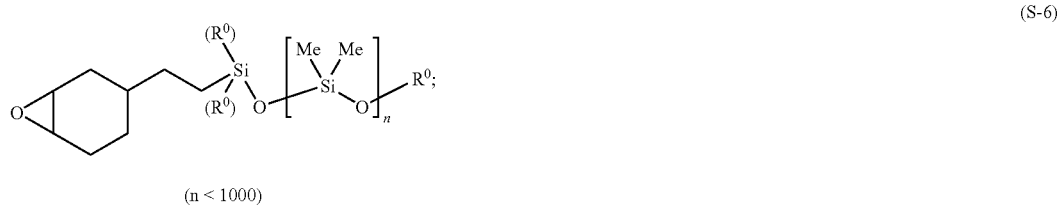
(S-6)
in which formulae R°, which may be identical or different, represents an alkyl, cycloalkyl or aryl radical;
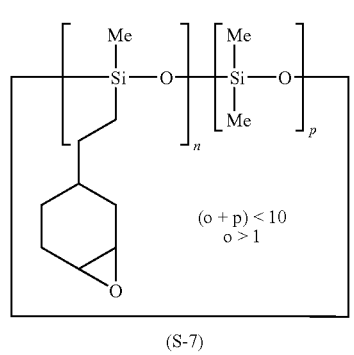
(S-7)
g)
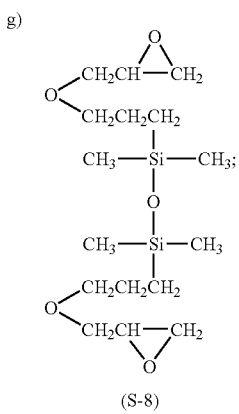
(S-8)
h)
i)
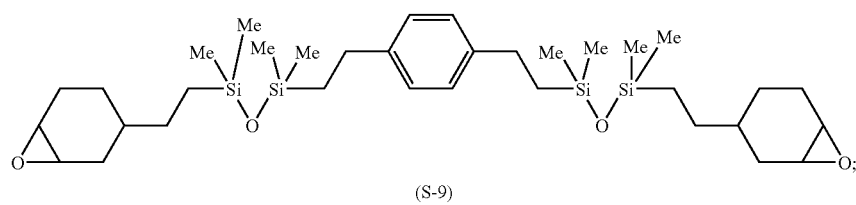
(S-9)

j)
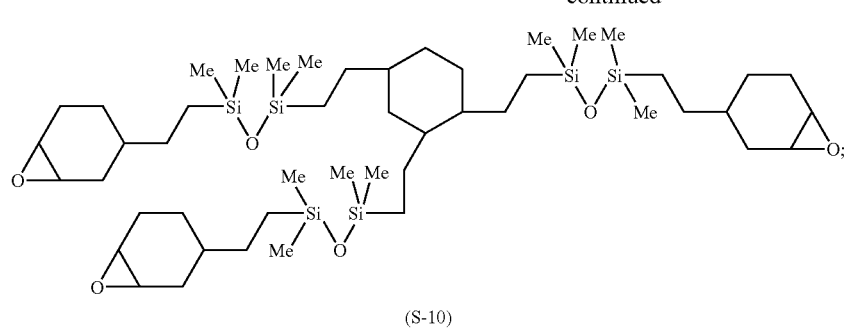
(S-10)
k)
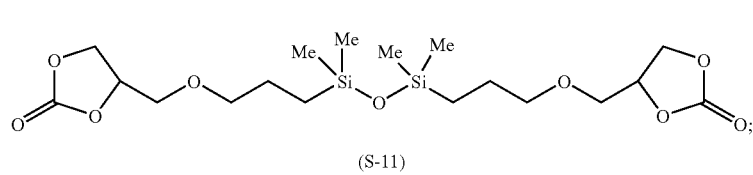
(S-11)
l)
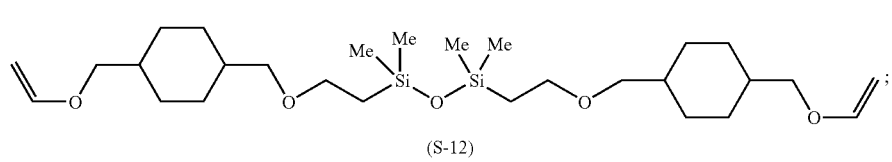
(S-12)
m)
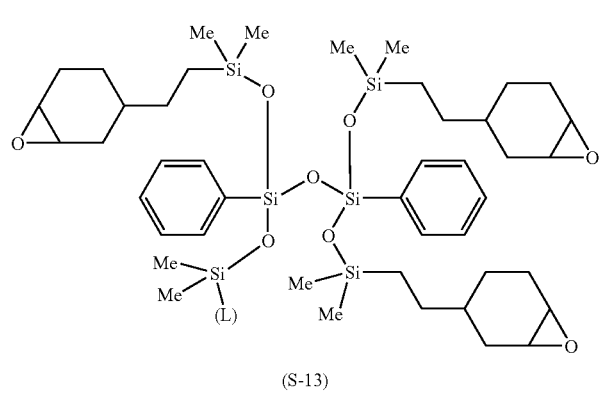
(S-13)
where L=H; OH; Me; Phenyl; $C_1$-$C_{12}$ Alkyl; $C_1$-$C_6$ Cycloalkyl;
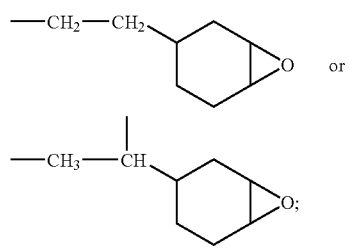
n)
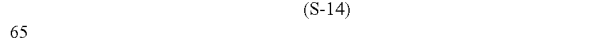
(S-14)
with n<100; a<100 and m<100: and o)

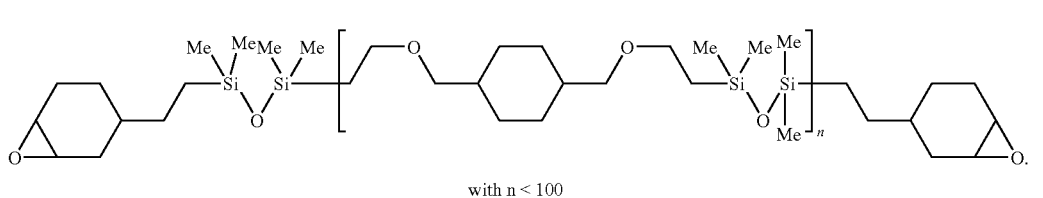

(S-15)

with n < 100

12. The dental composition as claimed in claim 11, wherein the cationically reactive compound (A) is selected from the group consisting of the compounds (S-1) to (S-15).

13. The dental composition as claimed in claim 1, wherein the cationically reactive compound (A) is a monomers and/or (co)polymer selected from the group consisting of:
epoxys, vinyl ethers, oxetanes, spiroorthocarbonates spiroorthoesters, and Combinations thereof.

14. The dental composition as claimed in claim 13, in which the cationically reactive compound (A) comprises at least one crosslinkable and/or polymerizable silicone oligomer (G-1) or silicone polymer (G-2), which is liquid at room temperature or thermofusible at a temperature below 100° C., and comprising:
a) at least one unit having the following formula:

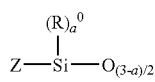

(M-13)

in which formula:
a=0, 1 or 2,
$R^0$, which may be identical or different, represents an alkyl, cycloalkyl, aryl, vinyl, hydrogeno or alkoxy radical,
Z, which may be identical or different, is an organic substituent comprising at least one oxirane, alkenyl ether, oxetane, dioxolane and/or carbonate function, and
b) at least two silicon atoms.

15. The dental composition as claimed in claim 14, wherein the unit (M-13) comprises groups Z selected from the group consisting of the radicals (R-1) to (R-9) below:

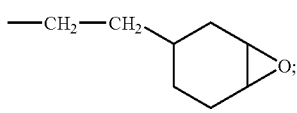
(R-1)

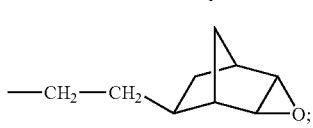
(R-2)

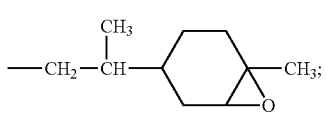
(R-3)

-continued

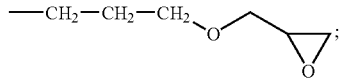
(R-4)

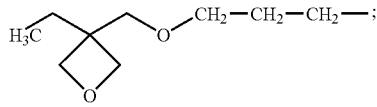
(R-5)

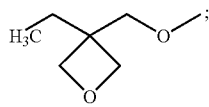
(R-6)

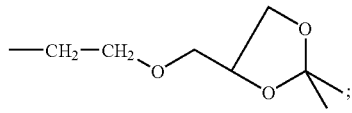
(R-7)

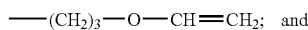
(R-8)

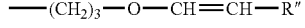
(R-9)

with R" representing a linear or branched $C_1$-$C_6$ alkyl radical.

16. The dental composition as claimed in claim 1, wherein the cationic photoinitiator (D) is a borate and is selected from those of the following formula in which:
a) the cationic species of the borate is selected from the group consisting of:
(1) the onium cations of formula:

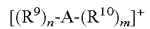 (I)

in which formula:
A represents an element from groups 15 to 17,
$R^9$ represents a $C_6$-$C_{20}$ carbocyclic or heterocyclic aryl radical, said heterocyclic radical possibly optionally containing nitrogen or sulfur as hetero elements,
$R^{10}$ represents $R^9$ or a linear or branched $C_1$-$C_{30}$ alkyl or alkenyl radical; said radicals $R^9$ and $R^{10}$ being optionally substituted with a $C_1$-$C_{25}$ alkoxy, $C_1$-$C_{25}$ alkyl, nitro, chloro, bromo, cyano, carboxyl, ester or mercapto group,
m and n are integers, with n+m=v+1, v being the valency of the element A,
(2) oxoisothiochromanium cations; and
(3) organometallic cations having the following formula:

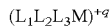 (II)

in which formula:
M represents a metal from groups 4 to 10 of the Periodic Table, L1 represents a ligand linked to the metal M via π electrons, the ligand being chosen from the ligands $\eta^3$-alkyl, $\eta^5$-cyclopentadienyl and $\eta^7$-cycloheptatrienyl and the $\eta^6$-aromatic compounds chosen from the optionally substituted $\eta^6$-benzene ligands and the compounds containing from 2 to 4 fused rings, each ring being capable of contributing to the valency layer of the metal M via 3 to 8 π electrons, L2 represents a ligand linked to the metal M via π electrons, the ligand being chosen from the $\eta^7$-cycloheptatrienyl ligands and the $\eta^6$-aromatic compounds chosen from the optionally substituted $\eta^6$-benzene ligands and the compounds containing from 2 to 4 fused rings, each ring being capable of contributing to the valency layer of the metal M via 6 or 7 π electrons, L3 represents from 0 to 3 identical or different ligands linked to the metal M via σ electrons, this or these ligand(s) being chosen from CO and $NO_2$+; the total electronic charge q of the complex toward which L1, L2 and L3 contribute and the ionic charge of the metal M being positive and equal to 1 or 2; and b) the anionic borate species of the formula:

$$[BX_aR_b]^- \quad (III)$$

in which formula:

a and b are integers ranging for a from 0 to 3 and for b from 1 to 4 with a+b=4, the symbols X represent:
  a halogen atom (chlorine or fluorine) with a=0 to 3, or
  an OH function with a=0 to 2, the symbols R are identical or different and represent:
  a phenyl radical substituted with at least one electron-withdrawing group, and/or with at least 2 halogen atoms, this being the case when the cationic species is an onium of an element from groups 15 to 17,
  a phenyl radical substituted with at least one element or an electron-withdrawing group, this being the case when the cationic species is an organometallic complex of an element from groups 4 to 10, or
  an aryl radical containing at least two aromatic groups, optionally substituted with at least one element or an electron-withdrawing group, irrespective of the cationic species.

17. The composition as claimed in claim 16, wherein the cationic photoinitiator (D) is selected from the group consisting of the following compounds:

(P-16):[($C_8H_{17}$)—O—$C_6H_4$—I—$C_6H_5$)]$^+$, [$B(C_6F_5)_4$]$^-$;
(P-17):[$C_{12}H_{25}$—$C_4$—I—$C_6H_5$]$^+$, [$B(C_6F_5)_4$]$^-$;
(P-18):[($C_8H_{17}$—O—$C_6H_4$)$_2$I]$^+$, [$B(C_6F_5)_4$]$^-$;
(P-19):[($C_8H_{17}$)—O—$C_6H_4$—I—$C_6H_5$)]$^+$, [$B(C_6F_5)_4$]$^-$;
(P-20):[($C_6H_5$)$_2$S—$C_6H_4$—O—$C_8H_{17}$]$^+$, [$B(C_6H_4CF_3)_4$]$^-$;
(P-21):[($C_{12}H_{25}$—$C_6H_4$)$_2$I]$^+$, [$B(C_6F_5)_4$]$^-$;
(P-22):[$CH_3$—$C_6H_4$—I—$C_6H_4$—CH($CH_3$)$_2$]$^+$, [$B(C_6F_5)_4$]$^-$;
(P-23):(η5-cyclopentadienyl)(η6-toluene)Fe$^+$, [$B(C_6F_5)_4$]$^-$;
(P-24):(η5-cyclopentadienyl)(η6-methyl-1-naphthalene)Fe$^+$, [$B(C_6F_5)_4$]$^-$;
(P-25):(η5-cyclopentadienyl)(η6-cumene)Fe$^+$, [$B(C_6F_5)_4$]$^-$;
(P-26):[($C_{12}H_{25}$—$C_6H_4$)$_2$I]$^+$, [$B(C_6H_3(CF_3)_2)_2$]$^-$;
(P-27):[$CH_3$—$C_6H_4$—I—$C_6H_4$—$CH_2CH(CH_3)_2$]$^+$, [$B(C_6F_5)_4$]$^-$;
(P-28):[$CH_3$—$C_6H_4$)—I—$C_6H_4$—$CH_2CH(CH_3)_2$]$^+$, [$B(C_6H_3(CF_3)_2)_4$]$^-$; and (P-29):[$CH_3$—$C_6H_4$—I—$C_6H_4$—CH($CH_3$)$_2$]$^+$, [$B(C_6H_3(CF_3)_2)_4$]$^-$.

18. The dental composition as claimed in claim 1, wherein the cationic photoinitiator (D) is an iodonium salt.

19. The dental composition as claimed in claim 1, in which the photosensitizer (E) comprises in its structure one or more substituted or unsubstituted aromatic nuclei having a residual light absorption of between 200 and 500 nm.

20. The dental composition as claimed in claim 19, in which the photosensitizer (E) is selected from the group consisting of anthracenes, thioxanthones, camphorquinones, phenanthrenequinones and mixtures thereof.

21. The dental composition as claimed in claim 20, in which the photosensitizer (E) is a salt of a thioxanthone substituted with at least one group comprising an ammonium function.

22. The dental composition as claimed in claim 21, wherein the associated anion of the salt of the thioxanthone substituted with at least one group comprising an ammonium function is selected from the following anions: a halide, $BF_4^-$, $PF_6^-$; $SbF_6^-$; the anion (III) of formula [$BX_aR_b$]$^-$ defined as claimed in claim 18, $R_fSO_3^-$; ($R_fSO_2$)$_3C^-$ and ($R_fSO_2$)$_2N^-$ with $R_f$ being a linear or branched alkyl radical substituted with at least one halogen atom.

23. The dental composition as claimed in claim 1, in which the photosensitizer (E), optionally in combination with at least one camphorquinone, a phenanthrenequinone and/or a substituted anthracene, has the formula:

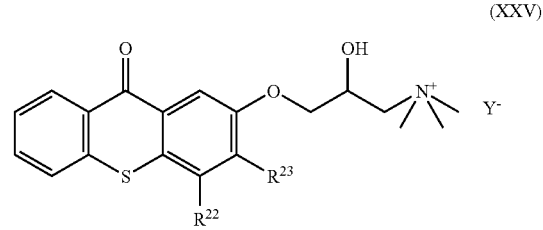

(XXV)

in which formula:

$R^{22}$ and $R^{23}$ are identical or different and represent a hydrogen or an optionally substituted $C_1$-$C_{10}$ alkyl radical, ($X^-$) being an anionic species, the anion (III) of formula [$BX_aR_b$]$^-$ defined as claimed in claim 16, $R_fSO_3^-$; ($R_fSO_2$)$_3C^-$ or ($R_fSO_2$)$_2N^-$, with $R_f$ being a linear or branched alkyl radical substituted with at least one halogen atom.

24. The dental composition as claimed in claim 1, in which the photosensitizer (E), optionally in combination with at least one camphorquinone, a phenanthrenequinone and/or a substituted anthracene, has the formula:

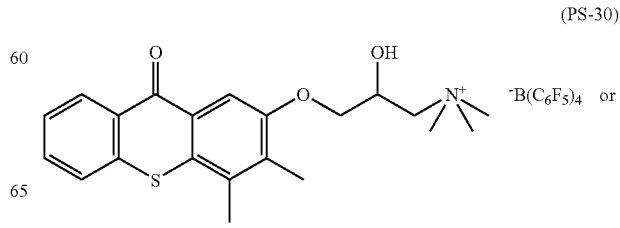

(PS-30)

-continued (PS-31)

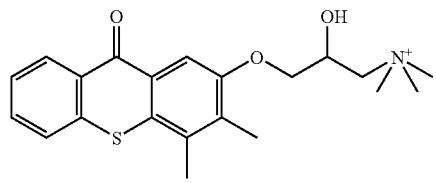

25. The dental composition as claimed in claim 1, in which the photosensitizer (E) is selected from the group consisting of the following compounds:
- (PS-30): 3-(3,4-dimethyl-9-oxo-9-thioxanthenen-2-yloxy)-2-hydroxypropyl)trimethylammonium chloride;
- (PS-31): 3-(3,4-dimethyl-9-oxo-9-thioxanthenen-2-yloxy)-2-hydroxypropyl)trimethylammonium tetrakis (pentafluorophenyl)borate;
- (PS-32): 3-(3,4-dimethyl-9-oxo-9-thioxanthenen-2-yloxy)-2-hydroxypropyl)trimethylammonium tetrakis (bis(trifluoromethyl)phenyl)borate;
- (PS-33): phenanthrenequinone;
- (PS-34): camphorquinone;
- (PS-35): acenaphthenequinone;
- (PS-36): dibenzoyl peroxide;
- (PS-37): 2-ethyl-9,10-dimethoxyanthracene;
- (PS-38): 9,10-diethoxyanthracene;
- (PS-39): 9,10-dibutoxyanthracene;
- (PS-40): 9-hydroxymethylanthracene;
- (PS-41): 2-dimethylaminothioxanthone;
- (PS-42): 3-ethylcarboxy-7-methoxythioxanthone;
- (PS-43): 1-phenylthio-4-propoxythioxanthone;
- (PS-44): 2-methoxythioxanthone;
- (PS-45): 2-(N,N-diethylaminopropoxy)thioxanthone;
- (PS-46): 2-isopropylthioxanthone;
- (PS-47): 1-chloro-4-propoxythioxanthone;
- (PS-48): 4-isopropylthioxanthone;

(PS-49)

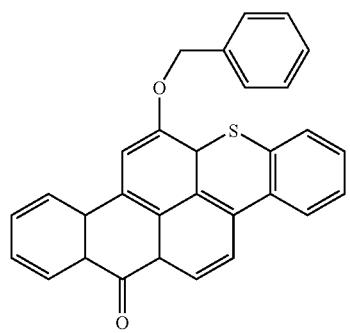

-continued (PS-50)

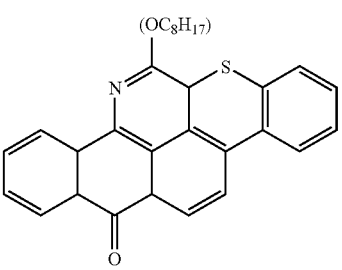

and mixtures thereof.

26. The dental composition as claimed in claim 1, in which the photosensitizer (E) is selected from the group consisting of the compounds of the coumarin, diketone, fluorone, amino ketone and para-aminostyryl ketone family, and also mixtures thereof.

27. The dental composition as claimed in claim 1, in which the dental filler (B) is a mineral glass or a combustion silica.

28. The dental composition as claimed in claim 1, in which the compound (G) is a silane (G-3) of formula:

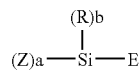

in which formula:

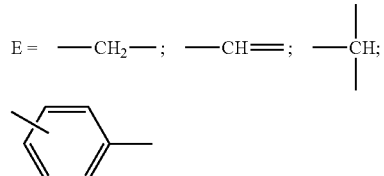

R, which may be identical or different, represents an alkyl, cycloalkyl, aryl, vinyl, hydrogeno or alkoxy radical, Z, which may be identical or different, is an organic substituent comprising at least one oxirane, alkenyl ether, oxetane and/or carbonate function, and a+b=3.

29. The dental composition as claimed in claim 28, in which the silane (G-3) is selected from the group consisting of the following molecules:

(S-93)

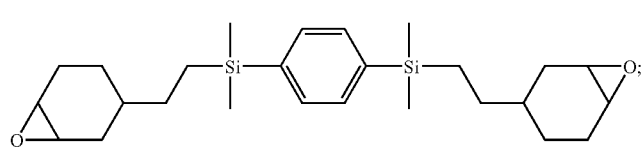

-continued
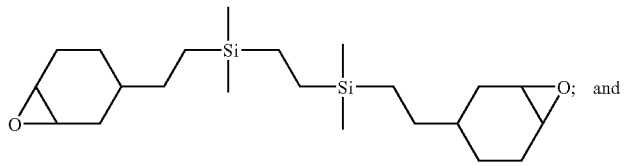
(S-94)
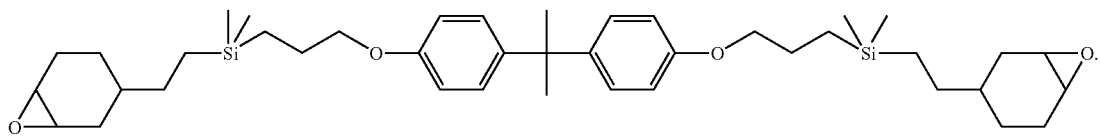
(S-95)
30. The dental composition as claimed in claim 1, in which the compound (G) is an organic compound (G-4) selected from the group consisting of the molecules:
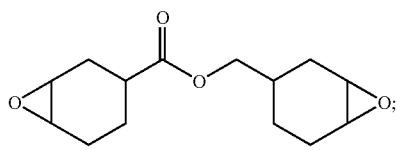
(S-96)
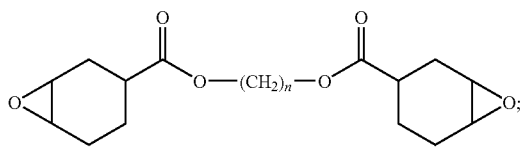
(S-97)
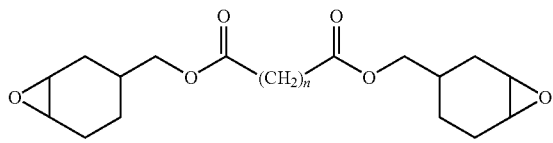
(S-98)
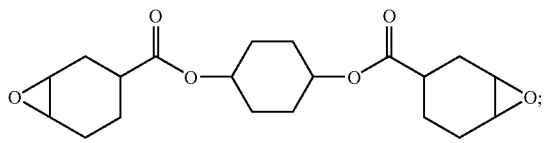
(S-99)
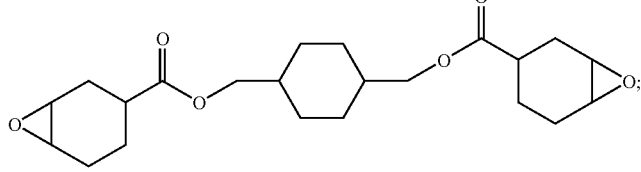
(S-100)
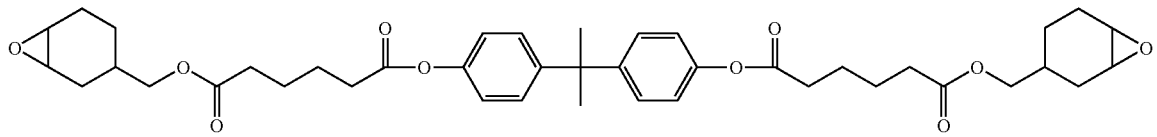
(S-101)
in which formulae: n is an integer between 1 and 10 (limits inclusive);
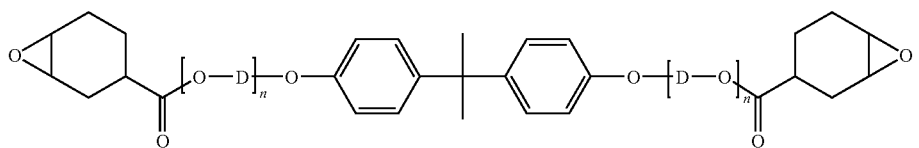
(S-103)
with n<100 and D=linear or branched $C_1$-$C_{12}$ alkylene; and

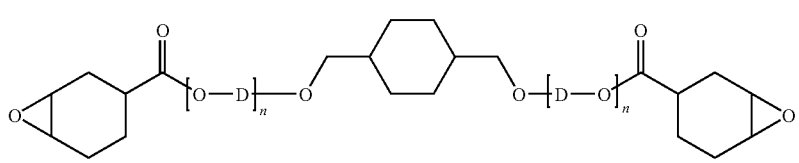

(S-104)

with n<100 and the group D=linear or branched $C_1$-$C_{12}$ alkylene.

31. A dental prosthesis obtained by crosslinking of a composition as claimed in claim 1.

32. Dental restoration material obtained by crosslinking of a composition as claimed in claim 1.

33. A process for treating a reinforcing filler which comprises the steps of:
   a) mixing in a solvent medium the at least one dental filler (B) with at least one organosilicon coupling agent (F) of the formula:

(F)

in which formula:

R is a hydrogen or a linear or branched $C_1$-$C_4$ alkyl radical, $R^1$ is a linear or branched alkyl radical or a phenyl radical, x is equal to 0, 1 or 2, and X is defined by one of the following formulae:

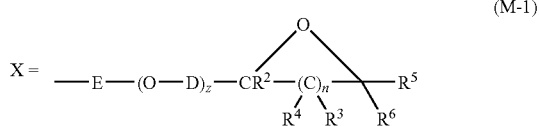

(M-1)

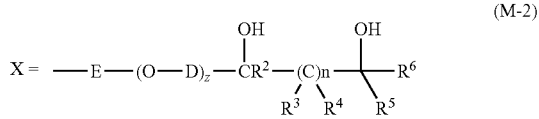

(M-2)

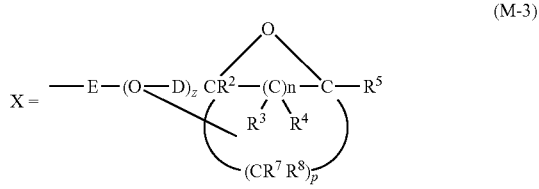

(M-3)

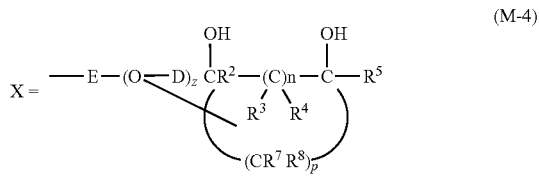

(M-4)

-continued

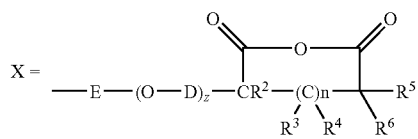

(M-5)

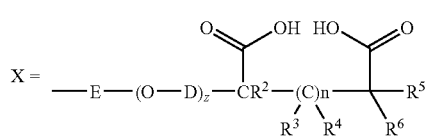

(M-6)

where:
E and D which are identical or different radicals chosen from linear or branched $C_{12}$-$C_{12}$ alkylene, z is equal to 0 or 1;

n is equal to 0 or 1;

p is equal to 0, 1, 2, 3, 4, 5 or 6;

$R^2$, $R^3$, $R^4$, $R^5$, $R^6$, $R^7$ and $R^8$ are radicals, which may be identical or different, representing a hydrogen or a linear or branched $C_1$-$C_{12}$ alkyl;

b) evaporating the solvent to obtain an intermediate dental filler (B-1),
   c) heat treating the intermediate dental filler (B-1) to allow the coupling reaction between the intermediate dental filler (B-1) and the coupling agent (F) and thus obtain an intermediate dental filler (B-2),
   d) mixing the intermediate dental filler (B-2) in a solvent medium with at least one compound (G) comprising at least one oxirane, oxetane, alkenyl ether and/or carbonate function,
   e) evaporating the solvent to obtain an intermediate dental filler (B-3), and
   f) heat treating the intermediate dental filler (B-3) to allow the reaction between the intermediate dental filler (B-3) and the compound (G) and thus to obtain a treated dental filler (B-4).

34. The process for treating a reinforcing filler as claimed in claim 33, in which the heat treating of the intermediate dental filler (B-1) and (B-3) in steps c) and f) of the process (I) is performed by heating the intermediate dental filler (B-1) and (B-3) to a temperature of less than or equal to 200° C.

35. The process for treating a reinforcing filler as defined in claim 33 in which the compound (G) comprises at least one function selected from the group consisting of the structures (M-7) to (M-12) below:

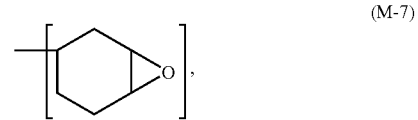

(M-7)

-continued
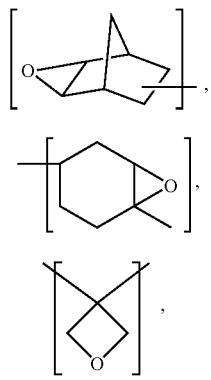
(M-8)
(M-9)
(M-10)
-continued
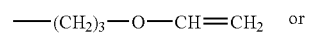 or (M-11)
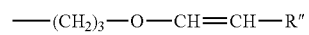 (M-12)
with R″ representing a linear or branched $C_1$-$C_6$ alkyl radical.
36. The process for treating a reinforcing filler as defined in claim 33, in which the reinforcing filler is a mineral glass or a combustion silica.
37. A reinforcing filler obtained via the process as claimed in claim 33.
* * * * *